United States Patent
Samadani

(10) Patent No.: US 12,348,841 B2
(45) Date of Patent: Jul. 1, 2025

(54) SYSTEMS AND METHODS FOR DETERMINING A MEASURE OF PHOTOBLEACHING OF A FLUORESCENCE TARGET

(71) Applicant: Intuitive Surgical Operations, Inc., Sunnyvale, CA (US)

(72) Inventor: Ramin Samadani, Menlo Park, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 206 days.

(21) Appl. No.: 18/120,129

(22) Filed: Mar. 10, 2023

(65) Prior Publication Data

US 2023/0300432 A1     Sep. 21, 2023

Related U.S. Application Data

(60) Provisional application No. 63/319,996, filed on Mar. 15, 2022.

(51) Int. Cl.
| | |
|---|---|
| H04N 23/10 | (2023.01) |
| A61B 1/06 | (2006.01) |
| G06T 7/13 | (2017.01) |
| G06T 7/174 | (2017.01) |

(52) U.S. Cl.
CPC .............. H04N 23/10 (2023.01); G06T 7/13 (2017.01); G06T 7/174 (2017.01); *A61B 1/0638* (2013.01)

(58) Field of Classification Search
None
See application file for complete search history.

(56) References Cited

U.S. PATENT DOCUMENTS

| | | | |
|---|---|---|---|
| 2013/0323673 A1* | 12/2013 | Hakomori | A61B 1/00009 433/29 |
| 2018/0157021 A1* | 6/2018 | Lytle | G02B 21/0076 |

OTHER PUBLICATIONS

Vertut, J, and Coiffet, P., "Robot Technology: Teleoperation and Robotics Evolution and Development," English translation, Prentice-Hall, Inc., Inglewood Cliffs, NJ, USA 1986, vol. 3A, 332 pages.

\* cited by examiner

*Primary Examiner* — Mark T Monk

(57) ABSTRACT

A fluorescence imaging control system may direct an imaging system to detect, over a period of time, first fluorescence emitted from a first fluorescing region illuminated with fluorescence excitation illumination. The first fluorescing region includes a first population of fluorophores that emit the first fluorescence. The fluorescence imaging control system may also direct the imaging system to detect, over the period of time, second fluorescence emitted from a second fluorescing region illuminated with the fluorescence excitation illumination. The second fluorescing region includes a second population of fluorophores that emit the second fluorescence. The first fluorescing region photobleaches at a first photobleaching rate and the second fluorescing region photobleaches at a second photobleaching rate that is different than the first photobleaching rate. The fluorescence imaging control system may determine, based on the detected first fluorescence and second fluorescence, a measure of photobleaching of the first fluorescing region.

19 Claims, 15 Drawing Sheets

SYSTEMS AND METHODS FOR DETERMINING A MEASURE OF PHOTOBLEACHING OF A FLUORESCENCE TARGET

RELATED APPLICATIONS

The present application claims priority under 35 U.S.C. § 119(e) to U.S. Provisional Patent Application No. 63/319,996, filed on Mar. 15, 2022, which is incorporated herein by reference in its entirety.

BACKGROUND INFORMATION

An imaging device (e.g., an endoscope) may be used during a surgical procedure to capture images of a surgical area associated with a patient. The images (e.g., a video stream) may be presented during the surgical procedure to assist the surgeon in performing the surgical procedure. In some scenarios, the images of the surgical area may be or be augmented with fluorescence images. Fluorescence images are generated based on detected fluorescence emitted by fluorophores when the fluorophores are excited by fluorescence excitation illumination. The fluorescence images may be used, for example, to highlight certain portions of the scene, certain types of tissue, or tissue perfusion of the surgical area in a selected color (e.g., green). A fluorescence target (e.g., a tissue phantom) that also fluoresces may be used at the surgical area to evaluate or assess fluorescence emitted from the surgical area. A fluorescence target may also be used to evaluate or assess operation of a fluorescence imaging system.

However, commonly used fluorophores, such as indocyanine green (ICG), photobleach over time due to prolonged exposure to fluorescence excitation illumination. Photobleaching is generally understood to be the chemical alteration of a fluorophore molecule caused by fluorescence excitation illumination such that the fluorophore molecule can no longer fluoresce. Thus, the intensity of fluorescence emitted by a group of fluorophores decreases with time as the fluorophores photobleach.

It is difficult, if not impossible, for a user to determine the extent of photobleaching of a fluorescence target and determine when the fluorescence target has exceeded its useful life. Attempts to address this problem have used fluorophores that photobleach less than conventional fluorophores, but there are problems with the cost, manufacturability, and size of these new fluorophores. In any event, these new fluorophores still photobleach. Thus, there is a need for improved apparatuses, systems, and methods for determining a measure of photobleaching of a fluorescence target.

SUMMARY

The following description presents a simplified summary of one or more aspects of the systems and methods described herein. This summary is not an extensive overview of all contemplated aspects and is intended to neither identify key or critical elements of all aspects nor delineate the scope of any or all aspects. Its sole purpose is to present one or more aspects of the systems and methods described herein as a prelude to the detailed description that is presented below.

An illustrative system may comprise a memory storing instructions and a processor communicatively coupled to the memory and configured to execute the instructions to direct an imaging system to detect, over a period of time, first fluorescence emitted from a first fluorescing region illuminated with fluorescence excitation illumination, the first fluorescing region comprising a first population of fluorophores that emit the first fluorescence, the first fluorescing region photobleaching at a first photobleaching rate; direct the imaging system to detect, over the period of time, second fluorescence emitted from a second fluorescing region illuminated with the fluorescence excitation illumination, the second fluorescing region comprising a second population of fluorophores that emit the second fluorescence, the second fluorescing region photobleaching at a second photobleaching rate that is different than the first photobleaching rate; and determine, based on the detected first fluorescence and second fluorescence, a measure of photobleaching of the first fluorescing region.

An illustrative fluorescence target may comprise a first fluorescing region comprising a first population of fluorophores that emit first fluorescence when the fluorescence target is illuminated with fluorescence excitation illumination, the first fluorescing region photobleaching at a first photobleaching rate; and a second fluorescing region proximate to the first fluorescing region and comprising a second population of fluorophores that emit second fluorescence when the fluorescence target is illuminated with the fluorescence excitation illumination, the second fluorescing region photobleaching at a second photobleaching rate that is different than the first photobleaching rate.

An illustrative method may comprise directing, by a fluorescence imaging control system, an imaging system to detect, over time, first fluorescence emitted from a first fluorescing region illuminated with fluorescence excitation illumination, the first fluorescing region comprising a first population of fluorophores that emit the first fluorescence, the first fluorescing region photobleaching at a first photobleaching rate; directing, by the fluorescence imaging control system, the imaging system to detect, over the period of time, second fluorescence emitted from a second fluorescing region illuminated with the fluorescence excitation illumination, the second fluorescing region comprising a second population of fluorophores that emit the second fluorescence, the second fluorescing region photobleaching at a second photobleaching rate that is slower than the first photobleaching rate; and determining, by the fluorescence imaging control system based on the detected first fluorescence and second fluorescence, a measure of photobleaching of the first fluorescing region.

An illustrative method of making a fluorescence target may comprise forming a first fluorescing region comprising a first population of fluorophores, the first fluorescing region configured to photobleach at a first photobleaching rate when illuminated over a period of time with fluorescence excitation illumination; and forming a second fluorescing region comprising a second population of fluorophores, the second fluorescing region configured to photobleach at a second photobleaching rate that is different than the first photobleaching rate when illuminated over the period of time with the fluorescence excitation illumination.

An illustrative system may comprise a memory storing instructions and one or more processors communicatively coupled to the memory and configured to execute the instructions to direct an imaging system to detect fluorescence emitted by fluorophores included in a fluorescence target illuminated with fluorescence excitation illumination; generate, based on the detected fluorescence, fluorescence image data representative of a fluorescence image; adjust, based on a measure of photobleaching of the fluorophores, the fluorescence image data; and provide the adjusted fluorescence image data for display by a display device.

BRIEF DESCRIPTION OF THE DRAWINGS

The accompanying drawings illustrate various embodiments and are a part of the specification. The illustrated embodiments are merely examples and do not limit the scope of the disclosure. Throughout the drawings, identical or similar reference numbers designate identical or similar elements.

DETAILED DESCRIPTION

Figure 1A:
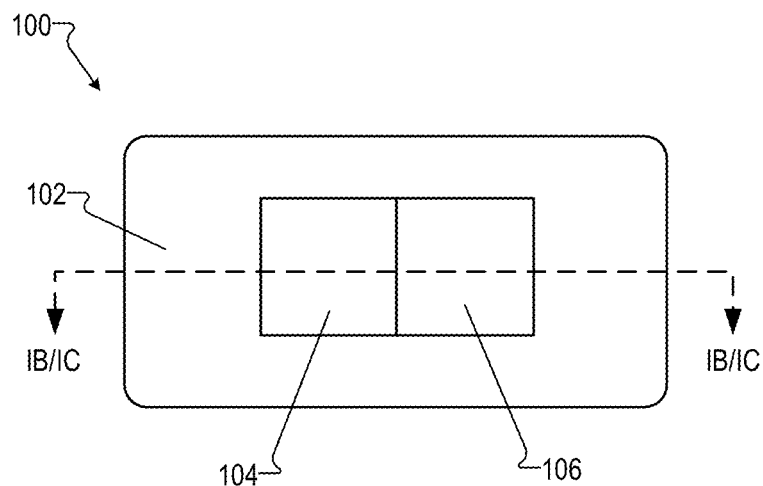
FIG. 1A shows a configuration of an illustrative fluorescence target.

Apparatuses, systems, and methods for determining a measure of photobleaching of a fluorescence target are described herein. Also described herein are apparatuses, systems, and methods for performing a photobleaching mitigation operation. In some implementations, a first fluorescing region having a first population of fluorophores and a second fluorescing region having a second population of fluorophores are illuminated with fluorescence excitation illumination, causing the first population of fluorophores to emit first fluorescence and the second population of fluorophores to emit second fluorescence. The first fluorescing region photobleaches at a first photobleaching rate and the second fluorescing region photobleaches at a second photobleaching rate that is slower than the first photobleaching rate. In some implementations, the different photobleaching rates of the first fluorescing region and the second fluorescing region is caused by an optical attenuator in the second fluorescing region that attenuates an intensity of the fluorescence excitation illumination incident on the second population of fluorophores so that the second photobleaching rate is slower than the first photobleaching rate. In additional or alternative implementations, the different photobleaching rates are caused by using, for the first population of fluorophores and the second population of fluorophores, different types of fluorophores having different photobleaching rates. In some implementations, the first fluorescing region and the second fluorescing region are part of a single fluorescence target.

A fluorescence imaging control system directs an imaging system (e.g., an endoscopic system) to detect, over a period of time, the first fluorescence and the second fluorescence emitted from the first fluorescing region and the second fluorescing region, respectively. The fluorescence imaging control system determines, based on the detected first fluorescence and second fluorescence, a measure of photobleaching of the first fluorescing region. The fluorescence imaging control system may also perform, based on the measure of photobleaching, a photobleaching mitigation operation, such as provide (e.g., display) an indication of the measure of photobleaching, adjust operation of the imaging system, and/or adjust a signal level of fluorescence image data representative of a fluorescence image depicting the first fluorescence.

The apparatuses, systems, and methods described herein provide various benefits. For example, a measure of photobleaching of a fluorescence target may be determined. The measure of photobleaching may be used to inform a user about the condition of the fluorescence target and/or a condition of a fluorescence image that is presently displayed. For instance, the user may be informed when the fluorescence target has exceeded its useful life. Additionally, the fluorescence signal of fluorescence images depicting the fluorescence target may be adjusted (e.g., digitally corrected) based on the measure of photobleaching of the fluorescence target to thereby reconstruct and render an ideal (e.g., unphotobleached) fluorescence target even when the fluorescence target has photobleached.

Various embodiments of the apparatuses, systems, and methods will be described in detail with reference to the figures. It will be understood that the embodiments described below are provided as non-limiting examples of how various novel and inventive principles may be applied in various situations. Additionally, it will be understood that other examples not explicitly described herein may also be captured by the scope of the claims set forth below. Apparatuses, systems, and methods described herein may provide one or more benefits that will be explicitly described or made apparent below.

FIG. 1A shows an illustrative configuration of a fluorescence target 100. Fluorescence target 100 may be used, for example, to test and/or calibrate operation of a fluorescence imaging system, to facilitate evaluation of fluorescence emitted from a scene (e.g., a surgical scene), and/or to assess tissue perfusion. In some examples, fluorescence target 100 is a tissue phantom having a composition, geometry, and/or optical properties that mimic a particular biological tissue of interest. Fluorescence target 100 may have any suitable shape and form, such as a card, a ruler, a plate, a sheet, a flexible material, a block, or a cylinder.

Fluorescence target 100 includes a substrate 102, a first fluorescing region 104 configured to emit first fluorescence, and a second fluorescing region 106 proximate to first fluorescing region 104 and configured to emit second fluorescence. As used herein, "proximate to" means that first fluorescing region 104 and second fluorescing region 106 are in direct contact with one another or are separated from one another (e.g., by a non-fluorescing region) but nevertheless are sufficiently close to one another that regions near the boundary between first fluorescing region 104 and second fluorescing region 106 are generally presumed to have the same exposure to fluorescence excitation illumination. Various different configurations of first fluorescing region 104 and second fluorescing region 106 will be described below in more detail.

As will be explained below, the first fluorescence emitted from first fluorescing region 104 may be used for evaluation and analysis purposes (e.g., evaluation or analysis of the fluorescence imaging system, of tissue, etc.). The second fluorescence emitted from second fluorescing region 106 is used as a reference by which a measure of photobleaching of first fluorescing region 104 may be determined. The measure of photobleaching of first fluorescing region 104 may be used to inform a user about the condition of fluorescence target 100 and/or about fluorescence images depicting fluorescence target 100.

Substrate 102 may be formed of any suitable solid material, including polymers, ceramics, composites, metals, or a combination thereof. Suitable polymers may include, without limitation, elastomers (e.g., silicone rubbers, natural rubbers, fluoroelastomers (such as polytetrafluoroethylene (PTFE), perfluoroether (PFA), fluorinated ethylene propylene (FEP)), ethylene propylene diene monomer (EPDM) rubbers, nitrile rubbers (e.g., acrylonitrile-butadiene rubber), and polyolefin elastomers), synthetic polymers (e.g., epoxy, resins, polyvinylchloride (PVC), polyethylene (PE), polyethylene glycol (PEG), polypropylene (PP), polymethylmethacrylate (PMMA), polystyrene (PS), polyurethanes (PU), polyamides, polyethyleneterephthalate (PET), glycol-modified PET, polysulfone, polyetherimide (PEI), polyethersulfone (PES), polyarylsulfone, polyetheretherketone (PEEK), polycarbonates, ethylene vinyl acetate (EVA), styrene butadiene copolymer (SBC), polylactic acid (PLA), polyglycolic acid (PGA), polycaprolactone (PCL), acrylics, acrylonitrile butadiene styrene (ABS), and cellulose acetate butyrate (CAB)), and natural polymers (e.g., rubber, carbohydrate polymers such as a polysaccharide (e.g., hyaluronic acid, chitosan, etc.), lipid polymers (e.g., triglycerides, triacylglycerols, triacylglycerides, phospholipids, waxes, etc.), and protein polymers (e.g., collagen, fibrin), etc.). Substrate 102 may be a single layer (e.g., a single material layer) or a lamination of multiple layers, which may be made of the same or different materials. It will be recognized that substrate 102 is merely optional, as fluorescence target 100 may be formed of only first fluorescing region 104 and second fluorescing region 106.

First fluorescing region 104 includes a first population of fluorophores configured to emit the first fluorescence. Second fluorescing region 106 includes a second population of fluorophores configured to emit the second fluorescence. When a fluorophore molecule in a ground state absorbs a photon of appropriate energy (fluorescence excitation illumination having a particular wavelength), the fluorophore molecule transitions to an excited state. When the excited fluorophore molecule returns to the ground state, the fluorophore molecule releases a photon of energy, thereby emitting fluorescence. The fluorophores in first fluorescing region 104 and second fluorescing region 106 may be any suitable type of fluorophore, including without limitation molecular dyes, organic dyes, proteins, IR-125, indocyanine green (ICG), fluorescein, rhodamine, quantum dots, organometallic complexes, lanthanides, fullerenes, nanotubes, nanoparticles, up-conversion materials, flavin adenine dinucleotide (FAD), reduced nicotinamide adenine dinucleotide (NADH), riboflavin, and/or collagen.

In some examples, the first population of fluorophores and the second population of fluorophores are the same type of fluorophore (e.g., ICG). Alternatively, the first population of fluorophores and the second population of fluorophores are different types of fluorophores. As will be explained below, different types of fluorophores may be used so that first fluorescing region 104 and second fluorescing region 106 photobleach at different rates.

First fluorescing region 104 and second fluorescing 106 may be formed in any suitable way. In some examples, the fluorophores are embedded, dissolved, absorbed, or doped in substrate 102, such as when substrate 102 is formed. In other examples, first fluorescing region 104 and second fluorescing region 106 are formed separately from substrate 102 and attached to substrate 102. For example, the fluorophores may be coated on substrate 102, adhered to substrate 102, or laminated as a separate layer on substrate 102. In some examples, the fluorophores are included in a fluorescent coating material configured for near-infrared coating of equipment (NICE).

In some examples, the fluorophores are combined with or in a support matrix (e.g., dissolved in a solvent), such as a biocompatible polymer (e.g., poly(methyl methacrylate) (PMMA), a polyurethane polymer, or any other suitable polymer), to produce a fluorescent mixture. The fluorescent mixture may also include other components, such as an absorbing agent (e.g., hem in) and/or a scattering agent (e.g., titanium oxide ($TiO_2$). The fluorescent mixture may be deposited or coated on substrate 102 and then cured.

For instance, first fluorescing region 104 and second fluorescing region 106 may each be formed from a liquid fluorescent mixture and cured into individual solid "tiles". The fluorescent mixture may be formed by dissolving the fluorophores (e.g., ICG) in a liquid polymer (e.g., a polyurethane polymer) or other solvent to form the fluorescent mixture. The fluorescent mixture may then be 3D printed or injection molded into the desired tile shape and cured to form solid tiles. The solid tiles may then be attached to substrate 102 (e.g., in recessed wells formed in substrate 102), such as by friction, an adhesive, or a mechanical fastener (e.g., a screw, snap fit, a cover layer on substrate 102, etc.). In other examples, the liquid fluorescent mixture may be deposited in recessed wells formed in substrate 102 and then cured within the wells. In yet further examples, first fluorescing region 104 and second fluorescing region 106 are not formed on a common substrate 102 but instead are formed on separate substrates that are joined or held together (temporarily or permanently) to form a single fluorescence target 100. The separate substrates may be held together rigidly or flexibly and may be held together in any suitable way, such as by an adhesive, an outer band or ring, a casing, hinges, joints, or fasteners. In examples in which fluorescence target 100 does not include substrate 102, first fluorescing region 104 and second fluorescing region 106 may be formed separately and held together, as just explained for separate substrates.

When fluorescence target 100 is subjected to prolonged exposure to fluorescence excitation illumination, the fluorophore molecules of the first fluorescing region 104 and second fluorescing region 106 may photobleach. Photobleaching of a fluorophore molecule is the irreversible chemical alteration of the fluorophore molecule that renders the fluorophore molecule unable to fluoresce when illuminated with fluorescence excitation illumination. A population of fluorophores (e.g., the first population of fluorophores in first fluorescing region 104 and the second population of fluorophores in second fluorescing region 106) photobleaches when the intensity of fluorescence emitted by the population of fluorophores decreases due to the increasing number of individual fluorophore molecules that have photobleached.

It may be useful to determine a measure of photobleaching of first fluorescing region 104 so that a user may know when fluorescence target 100 has passed its useful life. To this end, first fluorescing region 104 is configured to photobleach at a first photobleaching rate and second fluorescing region 106 photobleach is configured to photobleach at a second photobleaching rate that is slower than the first photobleaching rate when first fluorescing region 104 and second fluorescing region 106 have the same exposure to fluorescence excitation illumination. The different photobleaching rates of first fluorescing region 104 and second fluorescing region 106 enable determination of a measure of photobleaching of first fluorescing region 104, as will be explained below. First fluorescing region 104 and second fluorescing region 106 may be configured to have different photobleaching rates in any suitable way.

In some examples, second fluorescing region 106 includes an optical attenuator that attenuates an intensity of the fluorescence excitation illumination incident on the second population of fluorophores so that the second photobleaching rate is slower than the first photobleaching rate. While the optical attenuator attenuates an intensity of fluorescence excitation illumination incident on the second population of fluorophores, the optical attenuator does not attenuate an intensity of fluorescence excitation illumination that is incident on fluorescence target 100 at first fluorescing region 104 and at second fluorescing region 106, thereby ensuring that first fluorescing region 104 and second fluorescing region 106 are exposed over time to substantially the same intensity of fluorescence excitation illumination.

Figure 1B:
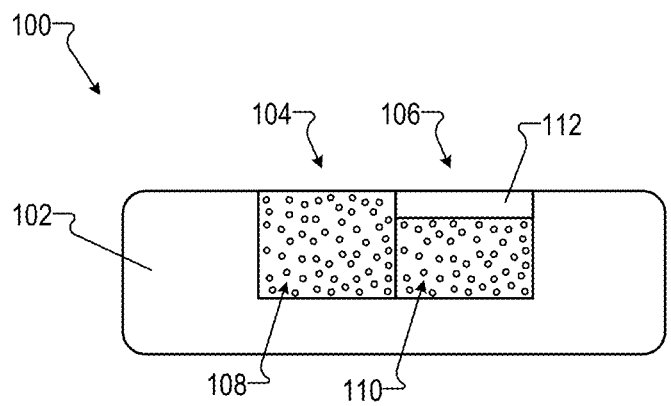
FIGS. 1B-1C show cross-sectional side views of various illustrative configurations of the fluorescence target of FIG. 1A having optical attenuators.

FIG. 1B shows a cross-sectional side view of an illustrative configuration of fluorescence target 100 having an optical attenuator. The cross-sectional view in FIG. 1B is taken along the dashed line labeled IB/IC in FIG. 1A. As shown in FIG. 1B, first fluorescing region 104 includes a first population of fluorophores 108 (represented by open circles) and second fluorescing region 106 has a second population of fluorophores 110 (also represented by open circles). Second fluorescing region 106 also includes a layer of an optical filter material 112 positioned over (e.g., on a light-incident side of) fluorophores 110. Optical filter material 112 attenuates an intensity of fluorescence excitation illumination that is incident on fluorophores 110. Optical filter material 112 may be implemented by any suitable material, such as a neutral density filter. While FIG. 1B shows only one layer of optical filter material 112, second fluorescing region 106 may have any number of layers of optical filter materials to achieve a desired level of attenuation of fluorescence excitation illumination. Moreover, in some examples (not shown), first fluorescing region 104 also includes a layer of light-transmissive non-filter material positioned over fluorophores 108 and having roughly the same thickness as optical filter material 112 to thereby ensure that first fluorescing region 104 and second fluorescing region 106 have roughly the same quantity of fluorophores 108 and 110.

Figure 1C:
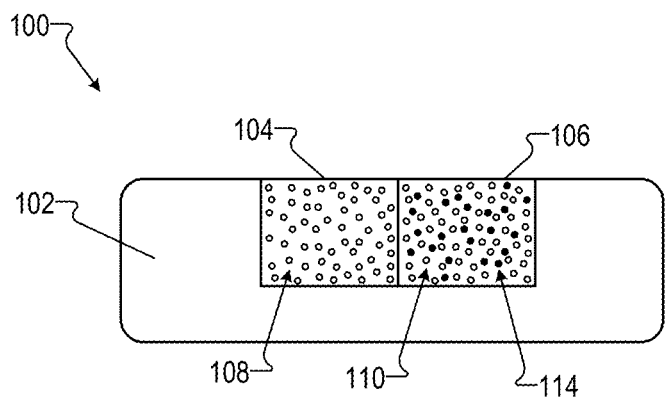

FIG. 1C shows a cross-sectional side view of another illustrative configuration of fluorescence target 100 having an optical attenuator in second fluorescing region 106. The cross-sectional view in FIG. 1C is taken along the dashed line labeled IB/IC in FIG. 1A. As shown in FIG. 1C, second fluorescing region 106 includes a light absorbing material 114 (represented by dark circles) within second fluorescing region 106. Light absorbing material 114 absorbs some of the fluorescence excitation illumination that would otherwise be scattered within second fluorescing region 106 and be incident on fluorophores 110. Thus, light absorbing material 114 attenuates an intensity of fluorescence excitation illumination that is incident on fluorophores 110. Light absorbing material 114 may be, for example, a light-absorbing pigment or dye embedded or doped within second fluorescing region 106. Light absorbing material 114 may be added to second fluorescing region 106 in any suitable manner, such as by adding light absorbing material 114 to the fluorescent mixture used to form second fluorescing region 106.

In some examples (not shown), second fluorescing region 106 may include both types of optical attenuators (e.g., a layer of optical filter material 112 and light absorbing material 114).

Additionally or alternatively to using an optical attenuator, the first population of fluorophores in first fluorescing region 104 and the second population of fluorophores in second fluorescing region 106 may be composed of different types of fluorophores that photobleach at different photobleaching rates. For example, first fluorescing region 104 may include a first population of a first type of fluorophores (e.g., ICG) and second fluorescing region 106 may include a second population of a second type of fluorophores (e.g., quantum dots) that photobleach slower than the first type of fluorophores. In this way, first fluorescing region 104 and second fluorescing region 106 have different photobleaching rates.

In the examples described above, first fluorescing region 104 and second fluorescing region 106 are part of the same fluorescence target 100. In alternative examples, first fluorescing region 104 and second fluorescing region 106 are each part of a separate fluorescence target. For example, first fluorescing region 104 may be part of a tissue phantom and second fluorescing region 106 may part of a separate fluorescence target (e.g., a target similar to fluorescence target 100 without first fluorescing region 104) that may be used when desired to check the photobleaching state of the tissue phantom. For instance, a user may selectively place the fluorescence target having only second fluorescing region 106 next to the tissue phantom to check the measure of photobleaching of the tissue phantom. The user may then remove the fluorescence target away from the tissue phantom, if desired. In the description that follows, discussion of implementations in which first fluorescing region 104 and second fluorescing region 106 are part of the same fluorescence target 100 may also be applied to implementations in which first fluorescing region 104 and second fluorescing region 106 are part of different fluorescence targets.

Figure 2:
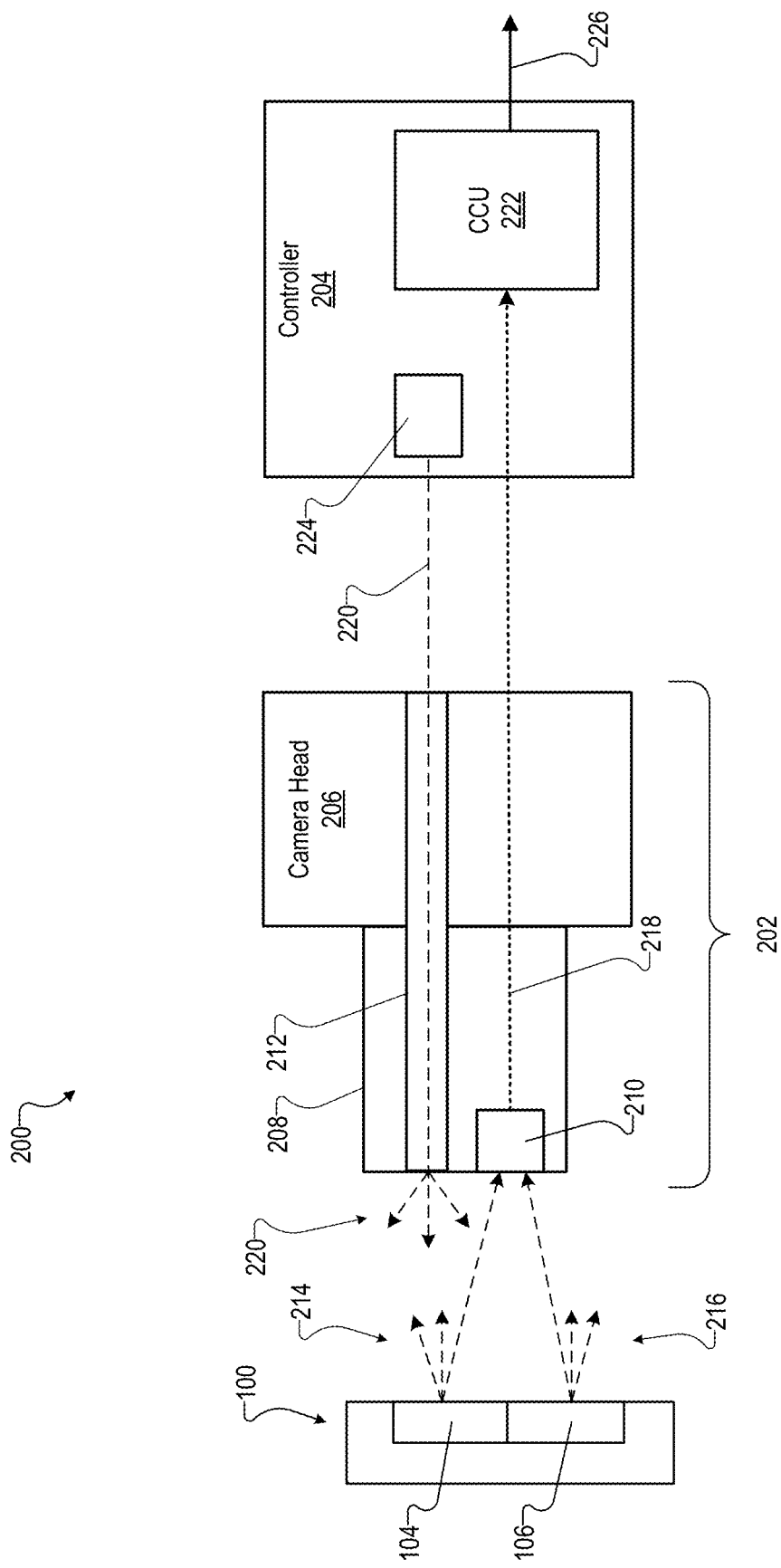
FIG. 2 shows an illustrative configuration of an imaging system configured to capture fluorescence images of a scene including the fluorescence target of FIGS. 1A-1C.

FIG. 2 shows an illustrative configuration of an imaging system 200 configured to capture fluorescence images of a scene including fluorescence target 100 and generate fluorescence image data representative of fluorescence images of the scene. As used herein, "fluorescence images" refers to images generated based on detected fluorescence and includes images generated based only on detected fluorescence as well as images generated based on both detected visible light and detected fluorescence (e.g., a visible light image augmented with fluorescence images (an "augmented image")). As shown, imaging system 200 includes an imaging device 202 and a controller 204. Imaging system 200 may include additional or alternative components as may serve a particular implementation, such as various optical and/or electrical signal transmission components (e.g., wires, lenses, optical fibers, choke circuits, waveguides, cables, etc.). While imaging system 200 shown and described herein is a fluorescence imaging system, imaging system 200 may alternatively include a fluorescence imaging system integrated with a visible light imaging system configured to capture visible light images of the scene. For example, the fluorescence imaging system and visible light imaging system may be physically integrated into the same physical components, or a standalone fluorescence imaging system may be inserted into an assistance port of a visible light endoscope.

Imaging device 202 may be implemented by any suitable device configured to capture fluorescence images of a scene. In some examples, as shown in FIG. 2, imaging device 202 is implemented by an endoscope. Imaging device 202 includes a camera head 206, a shaft 208 coupled to and extending away from camera head 206, a fluorescence detection sensor 210, and an illumination channel 212. Imaging device 202 may be manually handled and controlled (e.g., by a surgeon performing a surgical procedure on a patient). Alternatively, camera head 206 may be coupled to a manipulator arm of a computer-assisted surgical system and controlled using robotic and/or teleoperation technology. The distal end of shaft 208 may be positioned at or near the scene that is to be imaged by imaging device 202. For example, the distal end of shaft 208 may be inserted into a patient.

Fluorescence detection sensor 210 may be implemented by any suitable imaging sensor (e.g. a CCD image sensor or a CMOS image sensor) configured to detect (e.g., capture, collect, sense, or otherwise acquire) first fluorescence 214 emitted from first fluorescing region 104 and second fluorescence 216 emitted from second fluorescing region 106 and convert the detected fluorescence into fluorescence image data 218 representative of one or more fluorescence images. As shown, fluorescence detection sensor 210 is positioned at the distal end of shaft 208. Alternatively, fluorescence detection sensor 210 may be positioned closer to the proximal end of shaft 208, inside camera head 206, or outside imaging device 202 (e.g., inside controller 204). In these alternative configurations, optics included in shaft 208 and/or camera head 206 may convey fluorescence from the scene to fluorescence detection sensor 210.

Illumination channel 212 may be implemented by one or more optical components (e.g., optical fibers, light guides, lenses, etc.). As will be described below, fluorescence excitation illumination 220 may be provided to the scene by way of illumination channel 212 to illuminate the scene.

Controller 204 may be implemented by any suitable combination of hardware and/or software configured to control and/or interface with imaging device 202. For example, controller 204 may be at least partially implemented by a computing device included in a computer-assisted surgical system. Controller 204 includes a camera control unit ("CCU") 222 and an illumination source 224. Controller 204 may include additional or alternative components as may serve a particular implementation. For example, controller 204 may include circuitry configured to provide power to components included in imaging device 202. In some examples, CCU 222 and/or illumination source 224 are alternatively included in imaging device 202 (e.g., in camera head 206). CCU 222 is configured to receive and process fluorescence image data 218 from fluorescence detection sensor 210.

Illumination source 224 is configured to generate and emit fluorescence excitation illumination 220. Fluorescence excitation illumination 220 travels by way of illumination channel 212 to a distal end of shaft 208, where fluorescence excitation illumination 220 exits to illuminate the scene, including fluorescence target 100. Fluorescence excitation illumination 220 may include one or more broadband spectra of light or may include one or more discrete wavelengths of light.

To capture one or more fluorescence images of a scene, controller 204 (or any other suitable computing device) may activate illumination source 224 and fluorescence detection sensor 210. While activated, illumination source 224 emits fluorescence excitation illumination 220, which travels via illumination channel 212 to the scene. Fluorescence excitation illumination 220 causes first fluorescing region 104 to emit first fluorescence 214 and second fluorescing region 106 to emit second fluorescence 216. Fluorescence detection sensor 210 detects first fluorescence 214 and second fluorescence 216. Fluorescence detection sensor 210 (and/or other circuitry included in imaging device 202) convert the detected fluorescence into fluorescence image data 218 representative of one or more fluorescence images of the scene. Fluorescence image data 218 is transmitted via a wired or wireless communication link to CCU 222, which processes (e.g., packetizes and/or formats) fluorescence image data 218 and outputs processed fluorescence image data 226. CCU 222 may transmit processed fluorescence image data 226 to an image processor (not shown) for further processing.

The image processor may be implemented by one or more computing devices external to imaging system 200, such as one or more computing devices included in a computer-assisted surgical system. Alternatively, the image processor may be included in imaging system 200 (e.g., in controller 204). The image processor may prepare processed fluorescence image data 226 for display by one or more display devices (e.g., in the form of one or more still images and/or video streams). For example, the image processor may false-color fluorescing regions and/or selectively apply a gain to adjust (e.g., increase or decrease) the illumination intensity of the fluorescing regions. The image processor may also generate, based on processed fluorescence image data 226, a plurality of fluorescence images, which may be sequentially output to form a fluorescence video stream. Imaging system 200 may direct one or more display devices to display the fluorescence video stream. In some examples, the image processor may generate a graphical overlay based on fluorescence image data 226 and combine the graphical overlay with a visible light image to form an augmented image.

Figure 3A:
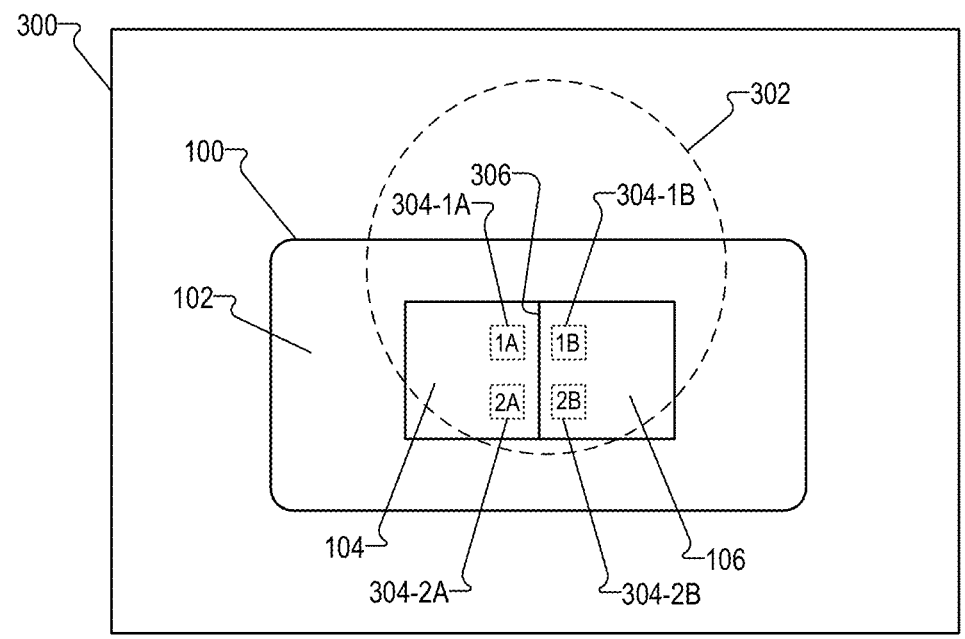
FIG. 3A shows an illustrative fluorescence image captured by an imaging device and depicting the fluorescence target of FIG. 1A as illuminated with fluorescence excitation illumination.

FIG. 3A shows an illustrative fluorescence image 300 captured by an imaging device (e.g., imaging device 202) and depicting fluorescence target 100 as illuminated with fluorescence excitation illumination (e.g., fluorescence excitation illumination 220). As shown in FIG. 3A, fluorescence target 100 is illuminated with fluorescence excitation illumination having a broad distribution pattern represented by the dashed-line circle 302, where the intensity of fluorescence excitation illumination is greater at the center of circle 302 than at the outer edges of circle 302. Within fluorescence image 300, a first position 304-1A corresponding to first fluorescing region 104 is positioned across a boundary 306 from a second position 304-1B corresponding to second fluorescing region 106. A first additional position 304-2A corresponding to first fluorescing region 104 is positioned across boundary 306 from a second additional position 304-2B corresponding to second fluorescing region 106. First position 304-1A and second position 304-1B, which are positioned near a center of circle 302, receive a higher intensity of fluorescence excitation illumination than first additional position 304-1B and second additional position 304-2B, which are positioned near the outer edge of circle 302.

Figure 3B:
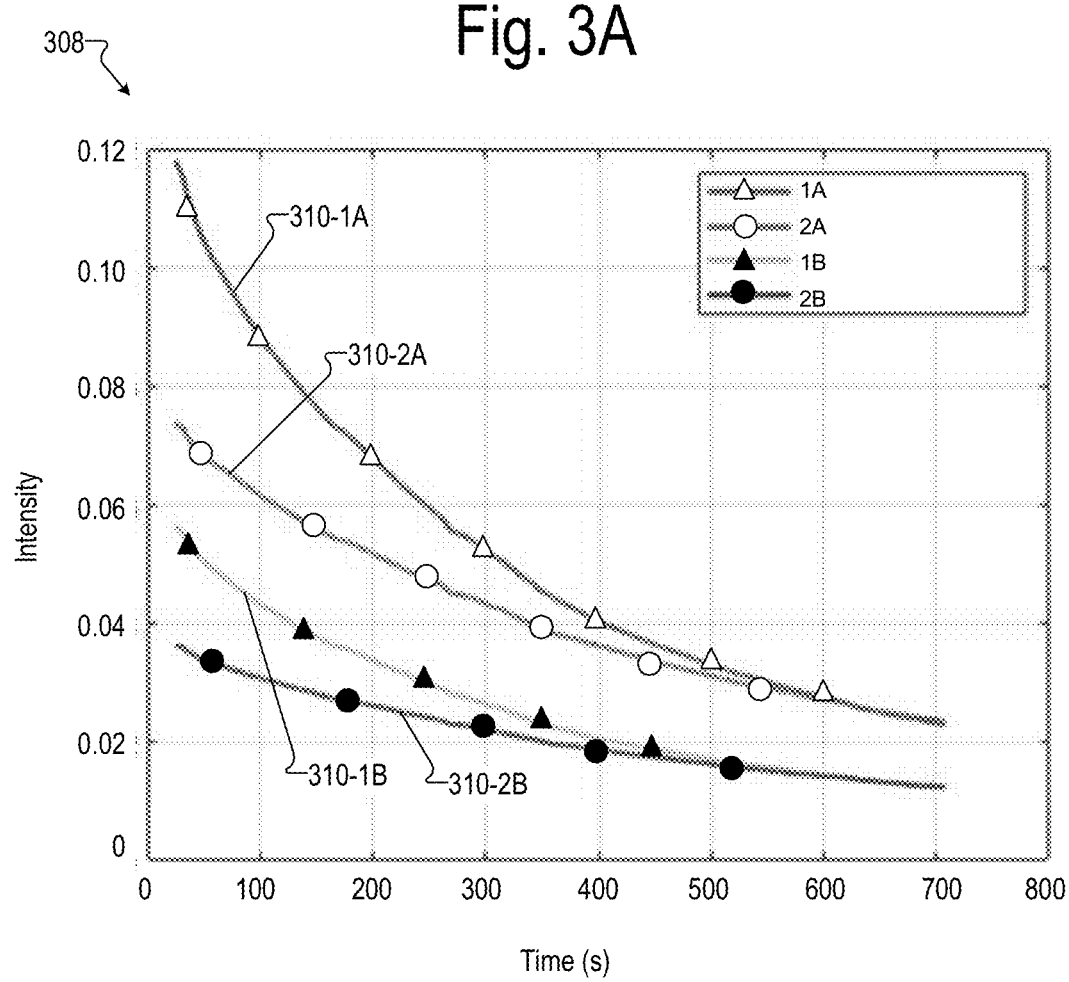
FIG. 3B shows an illustrative graph that plots intensity of detected fluorescence at various positions within the fluorescence image of FIG. 3A as a function of time.

FIG. 3B shows an illustrative graph 308 that plots intensity of detected fluorescence at positions 304 as a function of time. Graph 308 may be generated from a plurality of fluorescence images 300 captured over time (e.g., a fluorescence video stream). A first curve 310-1A (marked by open triangles) plots intensity of fluorescence detected from first position 304-1A, a second curve 310-1B (marked by closed triangles) plots intensity of fluorescence detected from second position 304-1B, a first additional curve 310-2A (marked by open circles) plots intensity of fluorescence detected from first additional position 304-2A, and a second additional curve 310-2B (marked by closed circles) plots intensity of fluorescence detected from second additional position 304-2B.

As evidenced by first curve 310-1A and second curve 310-1B, first fluorescing region 104 photobleaches with prolonged exposure to fluorescence excitation illumination 220. At some point in time, the intensity of first fluorescence 214 decreases beyond a desired or useful level. However, as can be seen by comparing first curve 310-1A with second curve 310-1B (and by comparing first additional curve 310-2A with second additional curve 310-2B), first fluorescing region 104 photobleaches faster than second fluorescing region 106. That is, the intensity of fluorescence emitted from first fluorescing region 104 decreases faster than the intensity of fluorescence emitted from second fluorescing region 106, assuming that first fluorescing region 104 and second fluorescing region 106 have the same exposure to fluorescence excitation illumination. As will be explained below, a fluorescence imaging control system exploits the differential photobleaching rates of first fluorescing region 104 and second fluorescing region 106 to determine a measure of photobleaching of first fluorescing region 104. The fluorescence imaging control system may perform a photobleaching mitigation operation based on the measure of photobleaching of first fluorescing region 104, such as provide an indication of the measure of photobleaching, adjust signal levels of fluorescence image data based on the measure of photobleaching to simulate an unphotobleached fluorescence target 100, and/or adjust an imaging system (e.g., adjust calibration parameters of imaging system 200 or any component thereof).

Figure 4:
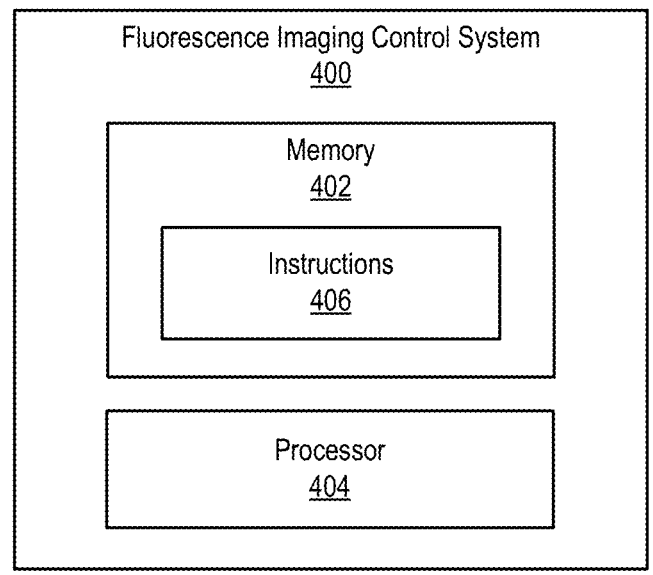
FIG. 4 illustrates an exemplary fluorescence imaging control system that may determine a measure of photobleaching of a first fluorescing region of the fluorescence target of FIG. 1A and perform a photobleaching mitigation operation.

FIG. 4 shows an illustrative fluorescence imaging control system 400 ("system 400") that may determine a measure of photobleaching of first fluorescing region 104 and perform a photobleaching mitigation operation. System 400 may be included in, implemented by, or connected to an imaging system, a surgical system, and/or a computing system described herein. For example, system 400 may be implemented, in whole or in part, by imaging system 200, a computer-assisted surgical system, and/or a stand-alone computing system communicatively coupled to an imaging system or a computer-assisted surgical system.

As shown, system 400 includes, without limitation, a memory 402 and a processing facility 404 selectively and communicatively coupled to one another. Memory 402 and processing facility 404 may each include or be implemented by hardware and/or software components (e.g., processors, memories, communication interfaces, instructions stored in memory for execution by the processors, etc.). For example, memory 402 and processing facility 404 may be implemented by any component in a computer-assisted surgical system. In some examples, memory 402 and processing facility 404 may be distributed between multiple devices and/or multiple locations as may serve a particular implementation.

Memory 402 may maintain (e.g., store) executable data used by processing facility 404 to perform any of the operations described herein. For example, memory 402 may store instructions 406 that may be executed by processing facility 404 to perform any of the operations described herein. Instructions 406 may be implemented by any suitable application, software, code, and/or other executable data instance. Memory 402 may also maintain any data received, generated, managed, used, and/or transmitted by processing facility 404.

Processing facility 404 may be configured to perform (e.g., execute instructions 406 stored in memory 402 to perform) various operations associated with determining a measure of photobleaching of first fluorescing region 104 and performing a photobleaching mitigation operation. Illustrative operations that may be performed by processing facility 404 are described herein. In the description that follows, any references to operations performed by system 400 may be understood to be performed by processing facility 404 of system 400. In some examples, system 400 directs an imaging system (e.g., imaging system 200) to detect, over a period time, first fluorescence and second fluorescence emitted from fluorescence target 100 illuminated with fluorescence excitation illumination. System 400 determines, based on the detected first fluorescence and second fluorescence, a measure of photobleaching of first fluorescing region 104. In some examples, system 400 determines, based on the first fluorescence and second fluorescence detected at a reference time and at a target time subsequent to the reference time, the measure of photobleaching of first fluorescing region 104. System 400 generates, based on the detected first fluorescence detected over the period of time, fluorescence image data representative of fluorescence images (e.g., fluorescence image data 218 or processed fluorescence image data 226) and provides the fluorescence image data for display by a display device.

In the examples that follow, a measure of photobleaching indicates a cumulative level of photobleaching of first fluorescing region 104 over a period of time from a reference time to a subsequent target time. That is, the measure of photobleaching may be indicative of the amount of the first population of fluorophores of first fluorescing region 104 that have photobleached over the period of time. The reference time may correspond to a non-photobleached state of first fluorescing region 104 (e.g., an initial time before the population of fluorophores have been exposed to any fluorescence excitation illumination). Alternatively, the reference time may correspond to a photobleached state of first fluorescing region 104 that is between the initial non-photobleached state and a current photobleached state. The target time may correspond to a current photobleached state of first fluorescing region 104. Alternatively, the target time may correspond to a photobleached state of first fluorescing region 104 that is between the initial non-photobleached state and a current photobleached state.

Figure 5:
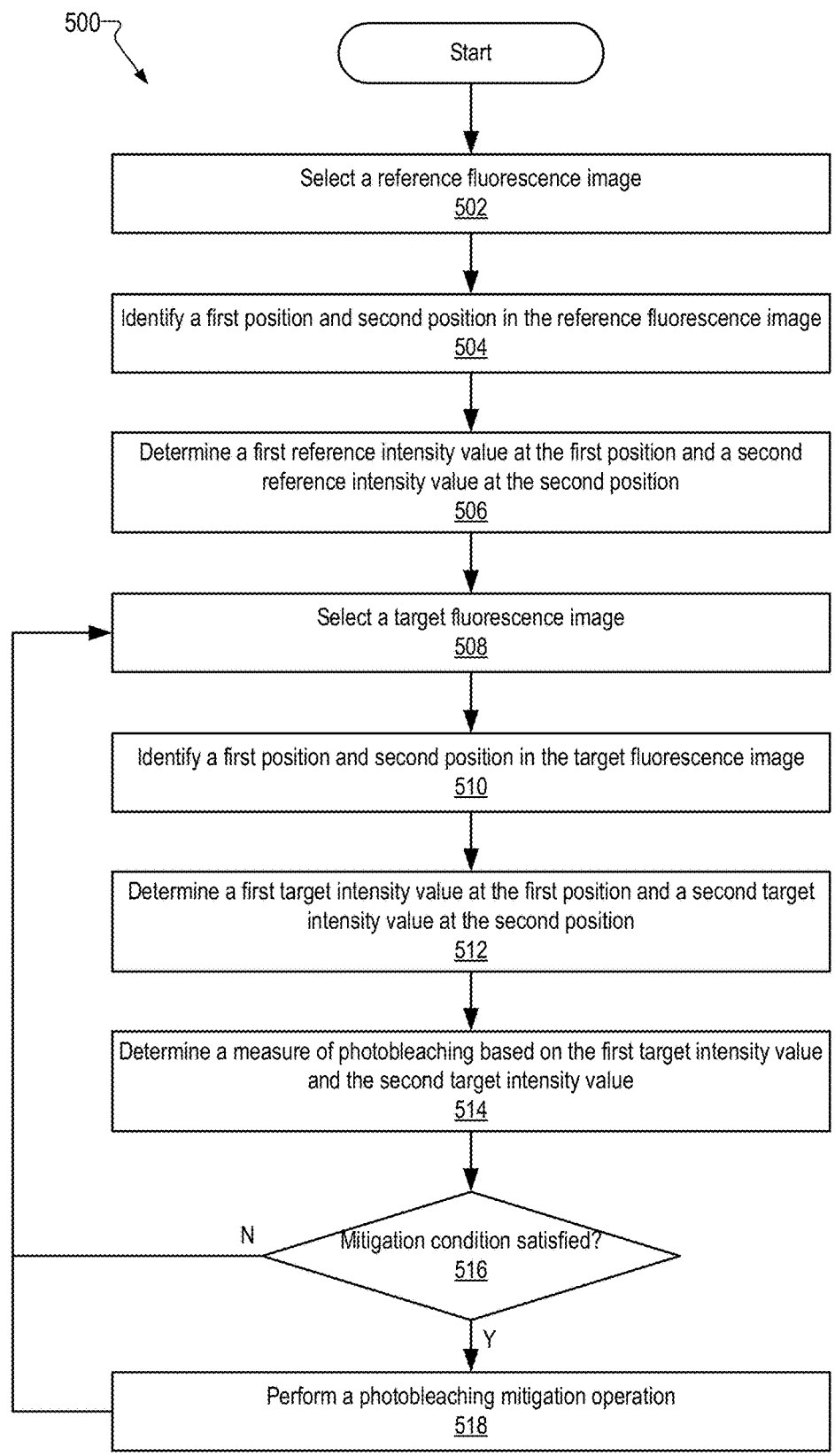
FIG. 5 shows an illustrative method of determining a measure of photobleaching of the first fluorescing region and performing, based on the measure of photobleaching, a photobleaching mitigation operation.

FIG. 5 shows an illustrative method 500 of determining a measure of photobleaching of first fluorescing region 104 and performing, based on the measure of photobleaching, a photobleaching mitigation operation. While FIG. 5 shows operations according to one embodiment, other embodiments may omit, add to, reorder, and/or modify any of the operations shown in FIG. 5. One or more of the operations shown in FIG. 5 may be performed by system 400, by any components included therein, and/or by any implementation thereof.

In operation 502, system 400 selects a reference fluorescence image for analysis of first fluorescence and second fluorescence. The reference fluorescence image is a fluorescence image used to establish reference fluorescence intensity values for first fluorescence and second fluorescence. The time at which the reference fluorescence image is captured is referred to herein as the "reference time." The reference fluorescence image is selected, for example, from fluorescence image data 218 and/or processed fluorescence image data 226. In some examples, the reference fluorescence image is the first image that captured the first fluorescence and second fluorescence emitted from fluorescence target 100. However, any other fluorescence image that captured the first fluorescence and second fluorescence may be selected as the reference fluorescence image. In some examples, the reference fluorescence image is based on a combination of a plurality of fluorescence images (e.g., a statistical average of multiple consecutive fluorescence images) that captured the first fluorescence and second fluorescence.

In operation 504, system 400 identifies, within the reference fluorescence image, a first reference position corresponding to (e.g., depicting) at least a portion of first fluorescing region 104 (e.g., first position 304-1A) and a second reference position corresponding to at least a portion of second fluorescing region 106 (e.g., second position 304-1B). The first reference position and the second reference position may each be an individual pixel or a group of pixels of the reference fluorescence image depicting at least a portion of first fluorescing region 104 and second fluorescing region 106, respectively. System 400 may identify the first reference position and the second reference position in any suitable manner.

In some examples, system 400 identifies the first reference position and the second reference position based on a boundary between first fluorescing region 104 and second fluorescing region 106 (e.g., boundary 306). In these examples, system 400 analyzes the reference fluorescence image with image processing and/or computer vision heuristics (e.g., algorithms, techniques, etc.) to detect the boundary between first fluorescing region 104 and second fluorescing region 106. For instance, system 400 may use edge detection heuristics to identify, in the reference fluorescence image, an edge of first fluorescing region 104 and/or an edge of second fluorescing region 106. System 400 may identify the first reference position and the second reference position to be at points (pixels or groups of pixels) a specified distance from the edge of the detected boundary or boundaries. When the specified distance is small, the first reference position and the second reference position may be assumed to have the same exposure to fluorescence excitation illumination over time.

Additionally or alternatively to detecting the boundary between first fluorescing region 104 and second fluorescing region 106, system 400 may identify the first reference position and/or the second reference position based on a shape of first fluorescing region 104 and/or second fluorescing region 106. For example, first fluorescing region 104 and/or second fluorescing region 106 may have a unique, predefined shape that may be configured to be detected by computer vision techniques (see, e.g., fluorescence target 1200C shown in FIG. 12C and described below in more detail). Upon detecting the predefined shape, system 400 may identify the first reference position and/or the second reference position as the group of pixels corresponding to the detected shape, or as a pixel or group of pixels within the detected shape.

In some examples, system 400 detects the boundary between (or a shape of) first fluorescing region 104 and second fluorescing region 106 by analyzing a reference visible light image or a reference augmented image with image processing and/or computer vision heuristics (e.g., edge detection heuristics). In these examples, fluorescence target 100 may include a fiducial or other marker visible under visible light (e.g., a boundary line) and that is configured to be detected using computer vision heuristics of system 400. System 400 may identify the first reference position and the second reference position to be at points (pixels) a specified distance from the edge of the detected boundary or boundaries in the visible light image or augmented image and map the first reference position and the second reference position to the corresponding reference fluorescence image.

In some examples, the position of fluorescence target 100 relative to imaging device 202 is predetermined (e.g., known prior to capturing the reference fluorescence image). In these examples, first fluorescing region 104 and second fluorescing region 106 are at the same image location each time fluorescence target 100 or another fluorescence target is imaged. For example, when imaging devices such as imaging device 202 are tested or calibrated, a fluorescence target 100 may be held in a holder in a fixed, constant position relative to the imaging device. In these examples, the first reference position and the second reference position may be a fixed location in the captured fluorescence images. Thus, system 400 may determine the first reference position and the second reference position without the use of computer vision techniques to detect a boundary or predefined shape by instead accessing (e.g., from memory 402) stored position information indicating the location of the first reference position and the second reference position.

In operation 506, system 400 determines, based on the reference fluorescence image, a first reference intensity value of the detected fluorescence at the first reference position and a second reference intensity value of the detected fluorescence at the second reference position. The first reference intensity value and the second reference intensity value may be determined in any suitable way. For example, the first and second reference intensity values may be the mean value, the median value, the maximum value, or the minimum value of the fluorescence signal level of all pixels in the first reference position and the second reference position, respectively.

In some examples, such as when second fluorescing region 106 includes an optical attenuator, the second reference intensity value is lower than the first reference intensity value. Accordingly, the first reference intensity value and/or the second reference intensity value may be adjusted to normalize the first reference intensity value and the second reference intensity value to a common intensity value. Thus, at the reference time, a ratio of the first reference intensity value to the second reference intensity value (the "reference intensity ratio") is one (1.0). Any suitable normalization scheme may be used. For example, the first reference intensity value and/or the second reference intensity value may each be independently scaled to a value of one, or any other common value. In some examples, the second reference intensity value is adjusted by a scaling factor to match the first reference intensity value. System 400 stores the selected scaling factor (e.g., in memory 402) to use again at a later time (a target time) to determine a measure of photobleaching of first fluorescing region 104.

In operations 502 to 508, system 400 determines the first reference intensity value and the second reference intensity value based on fluorescence detected from first fluorescing region 104 and second fluorescing region 106. In alternative examples, the first reference intensity value and the second reference intensity value may be predetermined (e.g., known prior to a first use of fluorescence target 100). For example, the first reference intensity value and the second reference intensity value may be known when fluorescence target 100 is first created. The first reference intensity value and the second reference intensity value may be determined in any suitable way, such as empirically through testing of one or more fluorescence targets 100. Accordingly, operations 502 to 506 may be omitted, and system 400 may instead obtain the first reference intensity value and the second reference intensity value, such as from memory 402, from a remote computing system (e.g., a remote server), or from user input. Additionally or alternatively, system 400 may obtain the first reference intensity value and the second reference intensity value by optically reading a preconfigured pattern (e.g., a barcode, a QR code, etc.) on fluorescence target 100 that encodes the first reference intensity value and the second reference intensity value.

In operation 508, system 400 selects a target fluorescence image captured at a target time occurring after the reference time. System 400 uses the target fluorescence image to determine a measure of photobleaching of first fluorescing region 104. The measure of photobleaching of first fluorescing region 104 represents a measure of photobleaching history of first fluorescing region 104 from the reference time to the target time. The target fluorescence image is selected, for example, from fluorescence image data 218 and/or processed fluorescence image data 226. The target fluorescence image may be any suitable fluorescence image captured after the reference fluorescence image, such as a most recent fluorescence image of a fluorescence video stream. However, any other fluorescence image that captured the first fluorescence and second fluorescence may be selected as the target fluorescence image. In some examples, the target fluorescence image is based on a combination of a plurality of fluorescence images (e.g., a statistical average of multiple consecutive fluorescence images) that captured the first fluorescence and second fluorescence.

In operation 510, system 400 identifies, within the target fluorescence image, a first target position corresponding to (e.g., depicting) at least a portion of first fluorescing region 104 and a second target position corresponding to second fluorescing region 106 for targeted analysis. The first target position and the second target position in the target fluorescence image may be identified in any suitable manner, including in any manner described above for identifying the first reference position and the second reference position. In some examples, the first target position and the first reference position correspond to (e.g., depict) the same portion of first fluorescing region 104, and the second target position and the second reference position correspond to the same portion of second fluorescing region 106.

In some situations, the position of fluorescence target 100 within the target fluorescence image may have moved or changed position as compared with the reference fluorescence image, such as after fluorescence target 100 and/or the imaging device has moved. Accordingly, the image processor and/or computer vision heuristics may be configured to track the first fluorescing region 104 and the second fluorescing region 106 over time (e.g., from the reference time to the target time) so that the first target position and the second target position correspond to the same location on first fluorescing region 104 and second fluorescing region 106 as the first reference position and second reference position.

In operation 512, system 400 determines, based on the target fluorescence image, a first target intensity value of the detected fluorescence at the first target position and a second target intensity value of the detected fluorescence at the second target position. The first target intensity value and the second target intensity value may be determined in any suitable way. For example, the first target intensity value and the second target intensity value may be the mean value, the median value, the maximum value, or the minimum value of the fluorescence signal level of all pixels in the first target position and the second target position, respectively.

If the first reference intensity value and/or the second reference intensity value was adjusted (e.g., normalized), as explained above regarding operation 508, system 400 also adjusts the second target intensity value and/or the first target intensity value in the same manner. For example, if system 400 adjusted the second reference intensity value to match the first reference intensity value by scaling the second reference intensity value by a scaling factor (e.g., two), system 400 similarly scales the second target intensity value by the same scaling factor.

In operation 514, system 400 determines a measure of photobleaching of first fluorescing region 104 based on the first target intensity value and the second target intensity value. In some examples, the measure of photobleaching is the ratio of the first target intensity value to the second target intensity value (the "target intensity ratio"). At the target time, first fluorescing region 104 will have photobleached more than second fluorescing region 106. Accordingly, the second target intensity value is greater than the first target intensity value, and thus the target intensity ratio is less than the reference intensity ratio. If the reference intensity ratio is one, the target intensity ratio is less than one.

In alternative examples, the measure of photobleaching is based on the target intensity ratio. For example, the measure of photobleaching may be a value on a scale from 0 to 100% that counts by a predetermined step range (e.g., 5%, 10%, etc.). For instance, if the target intensity ratio is 0.96, the measure of photobleaching may be 95%, indicating that the target intensity ratio is between 0.95 and 1.0. If the target intensity ratio is 0.72, the measure of photobleaching may be 70%, indicating that the target intensity ratio is between 0.70 and 0.75. It will be recognized that any suitable scale and step range may be used. In further examples, the measure of photobleaching may represent a degree to which first fluorescing region 104 has photobleached. For example, a target intensity ratio of 0.99 may indicate that first fluorescing region 104 has photobleached by 17% (e.g., a 17% reduction in detected fluorescence), and a target intensity ratio of 0.98 may indicate that first fluorescing region 104 has photobleached by 27% (e.g., a 27% reduction in detected fluorescence). Accordingly, system 400 may use the percent of photobleaching as the measure of photobleaching. System 400 may determine the percent of photobleaching in any suitable way, such as by reference to a lookup table or an algorithm that has been generated empirically.

In the examples described above, the measure of photobleaching is the target intensity ratio or another value based on the target intensity ratio and indicates a cumulative level of photobleaching of first fluorescing region 104 over a period of time from the reference time to the target time. In other examples, the measure of photobleaching of first fluorescing region 104 is an estimated remaining life of first fluorescing region 104. In these examples, system 400 is configured to estimate, based on the target intensity ratio, an estimated remaining life of first fluorescing region 104. System 400 may estimate the remaining life in any suitable ways. In some examples, system 400 assumes that first fluorescing region 104 will be exposed to the same level of fluorescence excitation illumination to which first fluorescing region 104 has been exposed up to the current point in time. Thus, system 400 assumes that the target intensity ratio decreases linearly over time (see FIG. 7, described below in more detail). Accordingly, system 400 estimates the remaining life based on the linear decrease of target intensity ratio (e.g., based on a linear algorithm). Alternatively, system 400 may estimate the remaining life based on a model (e.g., a machine learning model).

In operation 516, system 400 determines whether the measure of photobleaching satisfies a mitigation condition. If the mitigation condition is not satisfied, method 500 returns to operation 508 and repeats operations 508 to 516 based on another, subsequently-captured target fluorescence image (e.g., a fluorescence image captured after the previously analyzed target fluorescence image). On the other hand, if the mitigation condition is satisfied, method 500 proceeds to operation 518 in which system 400 performs a photobleaching mitigation operation and then returns to operation 508 for a subsequent target fluorescence image. It will be recognized that operation 516 may be omitted so that operation 518 follows operation 514. In this way, system 400 may continually perform a photobleaching mitigation operation based on the determined measure of photobleaching.

A mitigation condition is any suitable condition that may be used to determine when first fluorescing region 104 has photobleached such that a photobleaching mitigation operation is warranted. In some examples, the mitigation condition is satisfied when the measure of photobleaching determined in operation 514 is less than (or exceeds) a threshold value. For instance, if the measure of photobleaching is the target intensity ratio, the mitigation condition may be a target intensity ratio less than a threshold value (e.g., 0.75). Accordingly, if system 400 determines, in operation 516, that the target intensity ratio is less than the threshold value, system 400 performs, in operation 518, a photobleaching mitigation operation and then returns to operation 508 and repeats the process for a subsequent target fluorescence image. On the other hand, if system 400 determines that the target intensity ratio is not less than the threshold value, then system 400 returns to operation 508 and repeats the process for a subsequent target fluorescence image.

A photobleaching mitigation operation may include, for example, providing (e.g., displaying) an indication of the measure of photobleaching, modifying one or more fluorescence images based on the measure of photobleaching, and/or adjusting operation of a fluorescence imaging device or a fluorescence imaging system based on the measure of photobleaching (e.g., adjusting operating parameters of imaging system 200 during a calibration procedure). Illustrative photobleaching mitigation operations will be described below in more detail.

Figure 6:
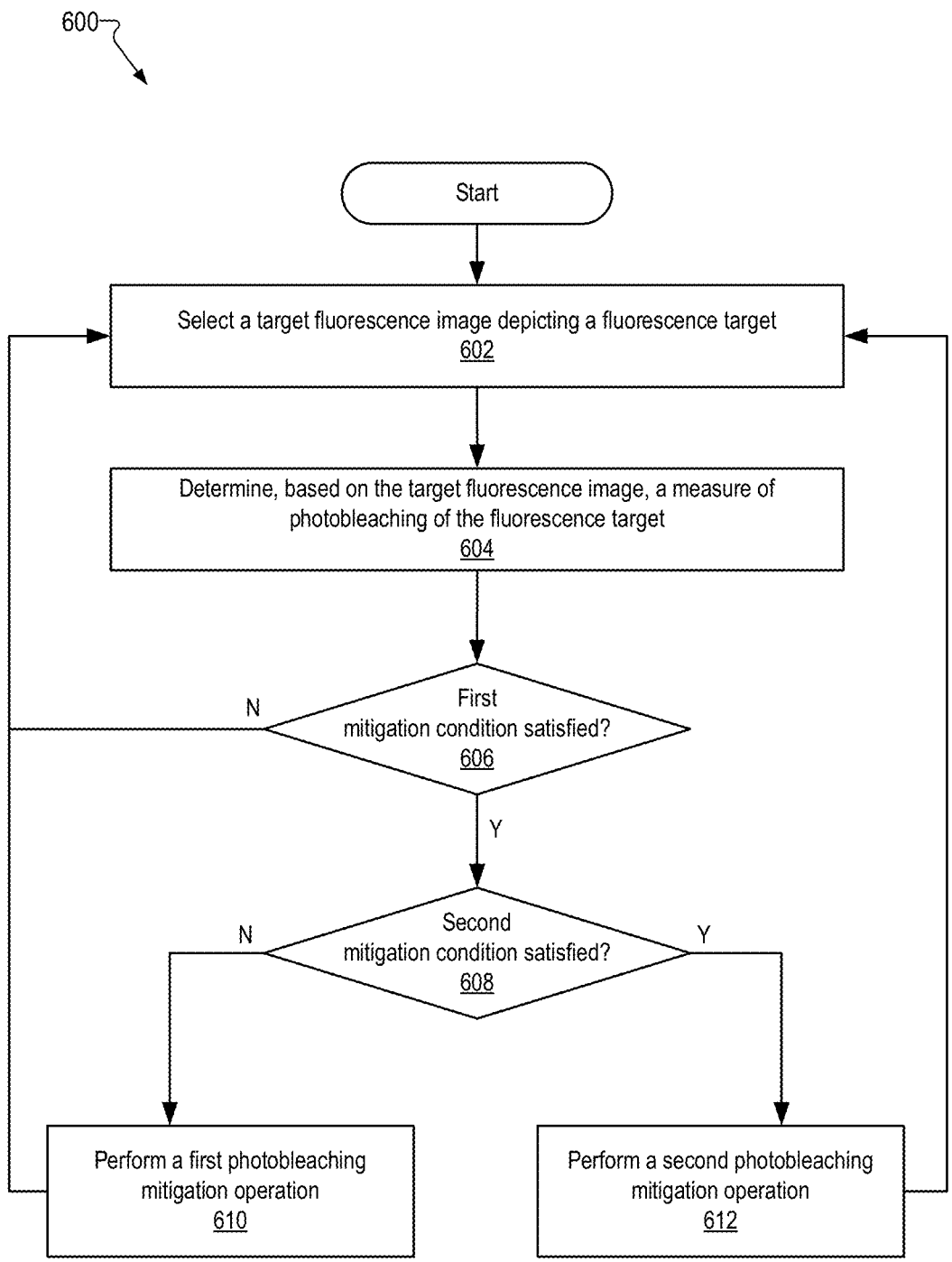
FIG. 6 shows an illustrative method in which the imaging system of FIG. 2 performs multiple photobleaching mitigation operations based on multiple different mitigation conditions.

While FIG. 5 shows that only one photobleaching mitigation operation is performed, any other number of photobleaching mitigation operations may be performed. FIG. 6 shows an illustrative method 600 in which system 400 performs multiple photobleaching mitigation operations based on multiple different mitigation conditions. While FIG. 6 shows operations according to one embodiment, other embodiments may omit, add to, reorder, and/or modify any of the operations shown in FIG. 6. One or more of the operations shown in FIG. 6 may be performed by system 400, by any components included therein, and/or by any implementation thereof.

In operation 602, system 400 selects a target fluorescence image depicting a fluorescence target (e.g., fluorescence target 100). Operation 602 may be performed in any manner described herein.

In operation 604, system 400 determines, based on the target fluorescence image, a measure of photobleaching of the fluorescence target (e.g., a measure of photobleaching of first fluorescing region 104 of fluorescence target 100). Operation 604 may be performed in any manner described herein.

In some examples, operations 602 and 604 are performed by performing operations 502 to 514 of method 500.

In operation 606, system 400 determines whether the measure of photobleaching determined in operation 604 satisfies a first mitigation condition. If the first mitigation condition is not satisfied, method 600 returns to operation 602 and repeats operations 602 and 604 based on a subsequently-captured target fluorescence image (e.g., a fluorescence image captured after the previously analyzed target fluorescence image). On the other hand, if the mitigation condition is satisfied, method 600 proceeds to operation 608.

In operation 608, system 400 determines whether the measure of photobleaching determined in operation 604 satisfies a second mitigation condition. If the second mitigation condition is not satisfied, method 600 proceeds to operation 610 in which system 400 performs a first photobleaching mitigation operation. Operation 610 may be performed in any manner described herein. Method 600 then returns to operation 602 and repeats operations 602 to 606 with another subsequently-captured target fluorescence image.

On the other hand, if the second mitigation condition is satisfied, method 600 proceeds to operation 612 in which system 400 performs a second photobleaching mitigation operation. Operation 612 may be performed in any manner described herein. Method 600 then returns to operation 602 and repeats operations 602 to 606 based on another subsequently-captured target fluorescence image.

In method 600 described above, system 400 performs either the first photobleaching mitigation operation (operation 610) or the second photobleaching mitigation operation (operation 612). In modifications of method 600, system 400 may perform both photobleaching mitigation operations if both mitigation conditions are satisfied. For example, operation 610 may follow operation 606 if the first mitigation condition is satisfied, and operations 608 and 612 may follow operation 610.

In the examples described above, operation 606 and operation 608 determine whether the measure of photobleaching satisfies a first mitigation condition or a second mitigation condition, respectively. Alternatively, the first mitigation condition and/or the second mitigation condition may be based on any other suitable attribute or parameter, such as a signal-to-noise ratio of the fluorescence image generated and/or provided for display.

In some modifications of method 600, a photobleaching mitigation operation may be performed without a determination that a mitigation condition is satisfied. For example, operation 606 may be omitted and operation 610 may follow after operation 604 (instead of after operation 608) so that a first photobleaching mitigation operation is performed based on the determined measure of photobleaching. If the second mitigation condition is satisfied (operation 608), system 400 performs the second photobleaching operation (operation 612) instead of, or in addition to, the first photobleaching operation. If the second mitigation condition is not satisfied, system 400 returns to operation 602 and/or performs a third photobleaching mitigation operation (not shown).

An illustrative operation of method 500 and method 600 will now be described using fluorescence image 300 of FIG. 3A and the data represented by first curve 310-1A and second curve 310-1B in FIG. 3B as examples. System 400 selects fluorescence image 300 captured at a reference time (about 10 seconds) as a reference fluorescence image. System 400 detects boundary 306 and identifies, within fluorescence image 300 and based on boundary 306, first position 304-1A as the first reference position and second position 304-1B as the second reference position. System 400 determines, based on the reference fluorescence image, that the first reference intensity value at the first reference position is 0.12 and the second reference intensity value at the second reference position is 0.06. System 400 normalizes the second reference intensity value to the first reference intensity value by scaling the second reference intensity value by a factor of two. Thus, the second reference intensity value, as adjusted, is 0.12. Accordingly, the reference intensity ratio (the ratio of the first reference intensity value to the second reference intensity value) is one (1.0).

At each of a plurality of different target times after the reference time, system 400 selects another fluorescence image 300 captured at a target time as a target fluorescence image. System 400 detects boundary 306 and identifies, within the target fluorescence image and based on boundary 306, first position 304-1A as the first target position and second position 304-1B as the second target position. System 400 determines, based on the target fluorescence image, the first target intensity value and the second target intensity value and adjusts the second target intensity value by a factor of two, as was previously done for the second reference intensity value.

Figure 7:
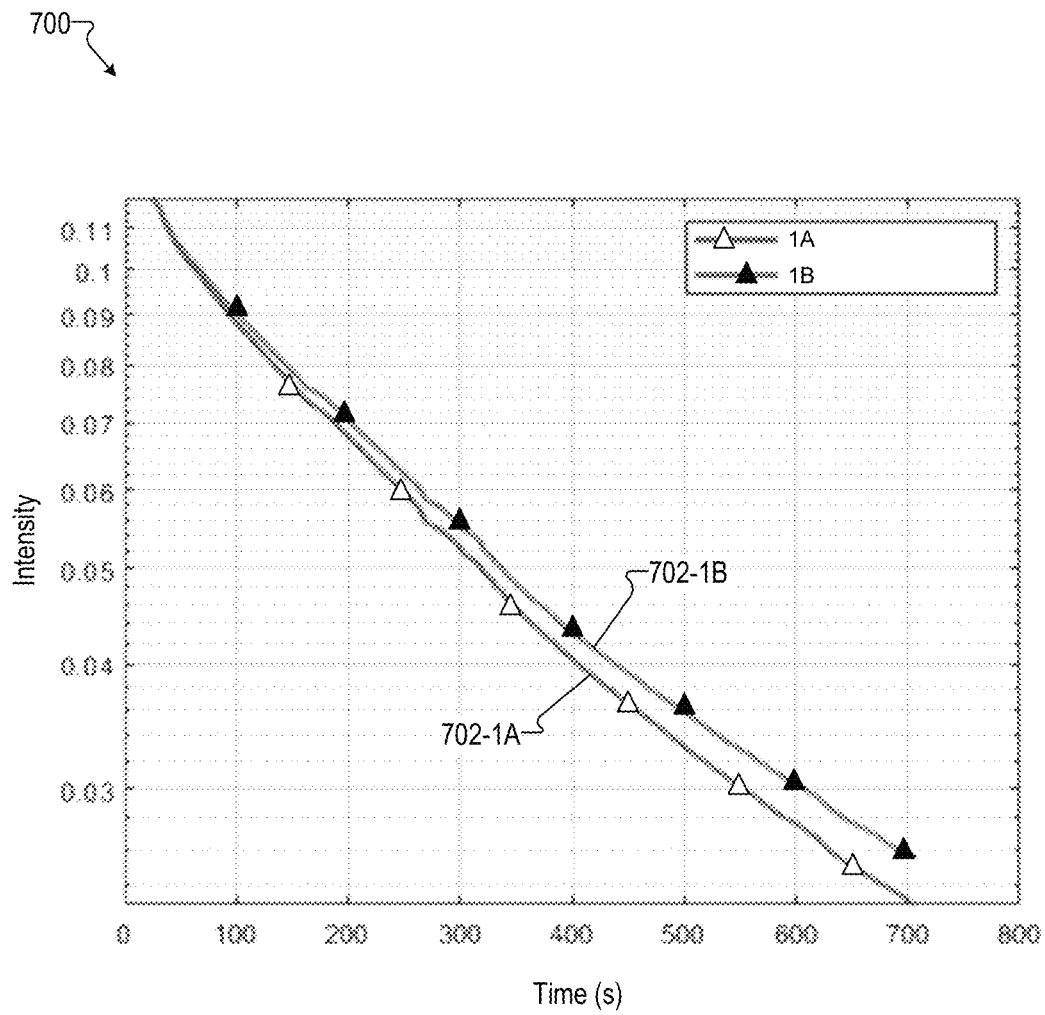
FIG. 7 shows an illustrative semi-log graph that plots detected fluorescence at a first position within a fluorescence image and detected fluorescence at a second position within the fluorescence image, as adjusted, as a function of time.

FIG. 7 shows an illustrative semi-log graph 700 that plots detected fluorescence at first position 304-1A and detected fluorescence at second position 304-1B, as adjusted (e.g., normalized), over time (e.g., at a plurality of target times). Graph 700 includes a first curve 702-1A (marked by open triangles) that plots intensity of fluorescence detected from first position 304-1A over time and a second curve 702-1B (marked by closed triangles) that plots intensity of fluorescence detected from second position 304-1B over time. First curve 702-1A corresponds to first curve 310-1A, and second curve 702-1B corresponds to second curve 310-1B scaled by a factor of two to normalize the second reference intensity value to the first reference intensity value.

At a target time of 100 seconds, system 400 determines, based on the target fluorescence image, that the first target intensity value at the first target position is 0.088 and the second target intensity value at the second target position is 0.045. System 400 adjusts the second target intensity value by scaling the second target intensity value by a factor of two, as was previously done for the second reference intensity value. Thus, the second target intensity value at the target time, as adjusted, is 0.90.

Figure 8:
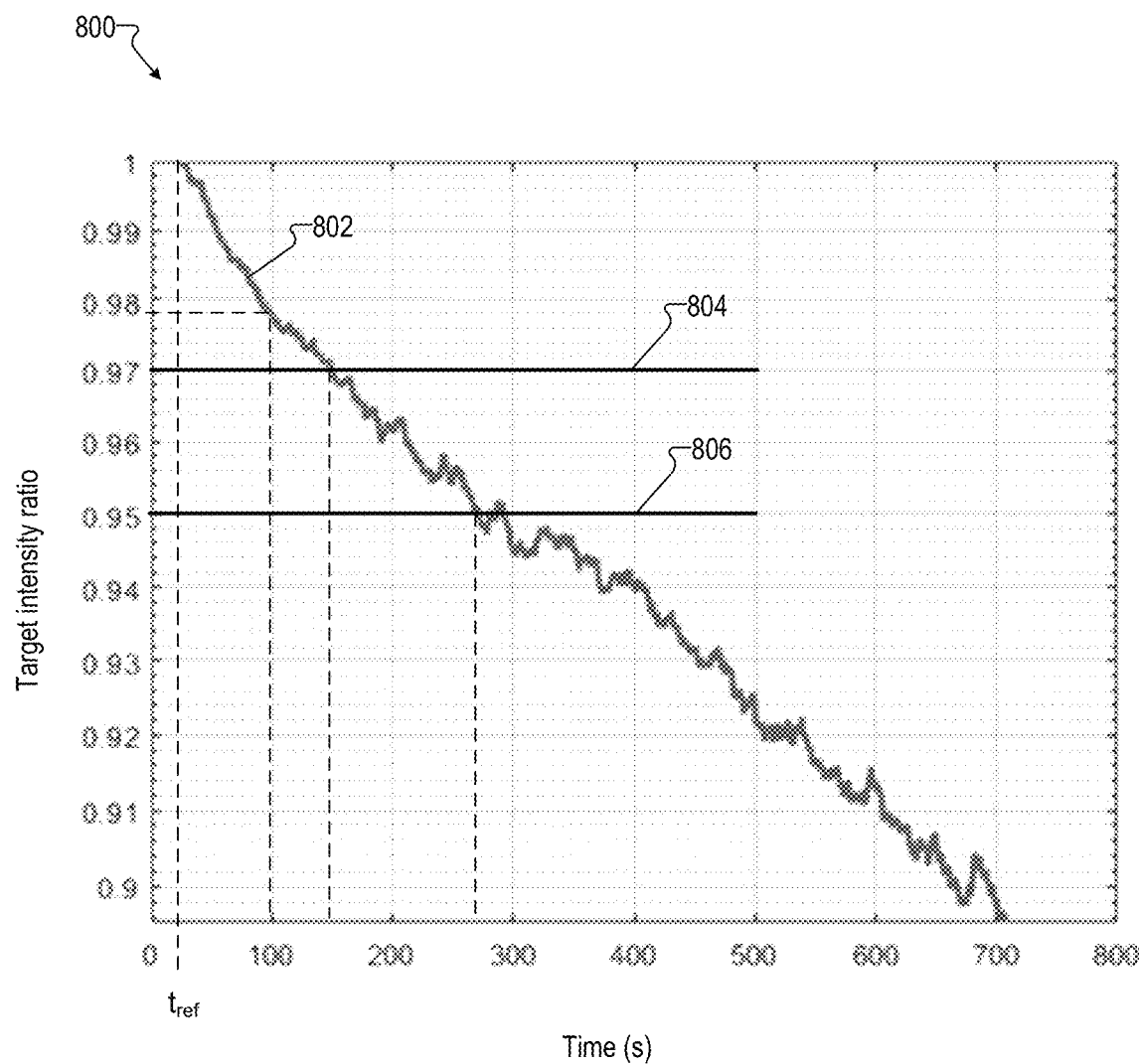
FIG. 8 shows an illustrative graph that includes a curve that plots a target intensity ratio as a function of time.

At each target time, system 400 determines the target intensity ratio based on the first target intensity value and the second target intensity value, as adjusted. FIG. 8 shows an illustrative graph 800 that plots, in a curve 802, the target intensity ratio as a function of time. As can be seen from curve 802, the target intensity ratio gradually decreases over time since first fluorescing region 104 is photobleaching faster than second fluorescing region 106. For example, at the reference time (10 seconds), the target intensity ratio is 1.0. At a target time of 100 seconds, the target intensity ratio is 0.978 (0.088 divided by 0.090). System 400 may use the target intensity ratio as the measure of photobleaching of first fluorescing region 104. In alternative examples, system 400 determines a measure of photobleaching based on the target intensity ratio.

When performing method 500 using the target intensity ratio as the measure of photobleaching, system 400 performs a first photobleaching mitigation operation (e.g., provides an indication of the measure of photobleaching of first fluorescing region 104) when the target intensity ratio reaches a first threshold value (e.g., when a mitigation condition is satisfied). As shown in FIG. 8, the first threshold value is 0.97, indicated by line 804. As indicated by curve 802, the target intensity ratio reaches the first threshold value at a time of about 150 seconds.

When performing method 600, system 400 performs a first photobleaching mitigation operation (e.g., adjusts signal values of pixels corresponding to first fluorescing region 104) when the target intensity ratio reaches the first threshold value (line 804) and performs a second photobleaching mitigation operation (e.g., provides a warning message to discontinue use of fluorescence target 100) when the target intensity ratio reaches a second threshold value. As shown in FIG. 8, the second threshold value is 0.95, indicated by line 806. As indicated by curve 802, the target intensity ratio reaches the second threshold value at a time of about 270 seconds.

It will be understood that the first threshold value and the second threshold value may each have any other value as may suit a particular implementation. Furthermore, in the examples just described with reference to FIG. 8, system 400 is configured to perform one or two photobleaching mitigation operations based on satisfaction of one or two mitigation conditions. However, in other examples system 400 may perform any other number (e.g., three or more) of photobleaching mitigation operations based on satisfaction of any other number (e.g., three or more) of mitigation conditions. Moreover, while FIGS. 3B, 7, and 8 show data plotted as graphs, system 400 may perform method 500 using the underlying raw data without generating the graphs.

Illustrative photobleaching mitigation operations that may be performed in response to a determination that a mitigation condition is satisfied will now be described. System 400 may perform a photobleaching mitigation operation by performing one or more operations configured to carry out the photobleaching mitigation operation and/or by directing one or more other computing devices (e.g., imaging system 200, an image processor, and/or a computer-assisted surgical system) to perform one or more computing operations configured to carry out the photobleaching mitigation operation.

In some examples, a photobleaching mitigation operation includes providing an indication of the measure of photobleaching determined in operation 514. The indication may have any form or format, such as a graphical (displayed)

indication, an audible indication (e.g., an audible warning message or warning tone), or a haptic indication (e.g., vibration of a user control device). A graphical indication may include any displayed element such as text (e.g., a numerical value, such as the target intensity ratio, and/or a warning message) and/or a graphical element (e.g., a warning icon, cross-hatching, and/or false-coloring). In some examples, the graphical indication may be superimposed on displayed fluorescence images (e.g., superimposed on a view of first fluorescing region 104). In some examples, the graphical indication may be interactive so that a user may interact with the graphical element to view additional information. For example, a user may manipulate a cursor or an object at the scene (e.g., a real or virtual surgical instrument) to select the graphical element. In response, system 400 may provide (e.g., in a popup message bubble or elsewhere) an indication of the measure of photobleaching or other information (e.g., an estimated remaining life of fluorescence target 100). In further examples, system 400 may turn ON and OFF the graphical indication, thus causing the graphical element to "blink" or "flash". Illustrative graphical indications will now be described with reference to FIGS. 9A to 10B.

Figure 9A:
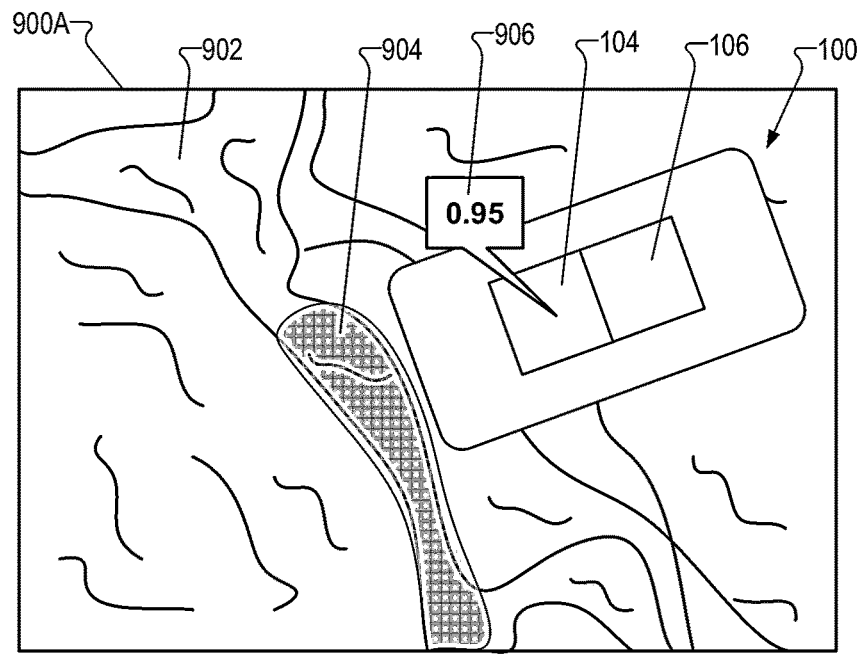
FIGS. 9A-9B and 10A-10B show various different illustrative images that include a displayed indication of the measure of photobleaching.

FIG. 9A shows an illustrative fluorescence image 900A that includes a displayed indication of the measure of photobleaching. In the example of FIG. 9A, fluorescence image 900A is an augmented image comprising a visible light image of a surgical scene including tissue 902 and fluorescence target 100 augmented with fluorescing regions (shown in grayscale). Fluorescence image 900A depicts fluorescence from fluorescing region 904 of tissue 902 and from first and second fluorescing regions 104 and 106 of fluorescence target 100. While fluorescence image 900A shows fluorescence target 100 within a body of a subject, fluorescence image 900A may depict fluorescence target 100 at any other scene, such as a scene external to a body (e.g., when calibrating an imaging system). Moreover, fluorescence image 900A may alternatively be a fluorescence only image that shows only fluorescing regions of the scene and does not show visible light components of the scene.

Fluorescence image 900A shows a message bubble 906 that points to first fluorescing region 104 and indicates the measure of photobleaching (e.g., the target intensity ratio) of first fluorescing region 104. Message bubble 906 may be displayed at any other suitable location as may serve a particular implementation. In alternative examples, the textual indication of the measure of photobleaching may be superimposed directly on first fluorescing region 104 rather than in message bubble 906.

Figure 9B:
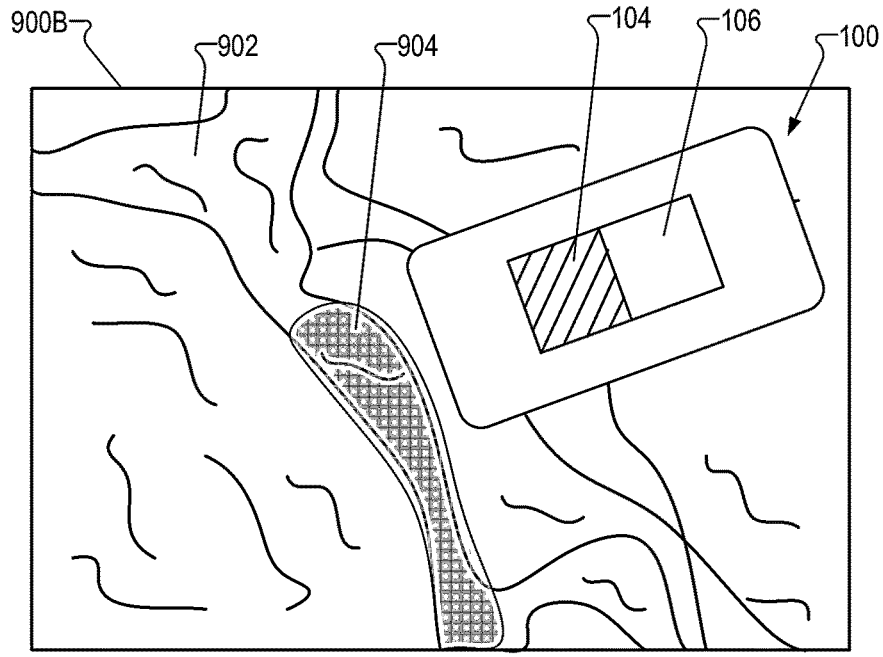

FIG. 9B shows another illustrative fluorescence image 900B that includes a displayed indication of the measure of photobleaching. Fluorescence image 900B is similar to fluorescence image 900A except that, in fluorescence image 900B, cross-hatching is superimposed on first fluorescing region 104 to indicate that first fluorescing region 104 has photobleached beyond a threshold level. It will be recognized that other graphical elements may be used instead of, or in addition to, cross-hatching, such as stippling or some other pattern.

Figure 10A:
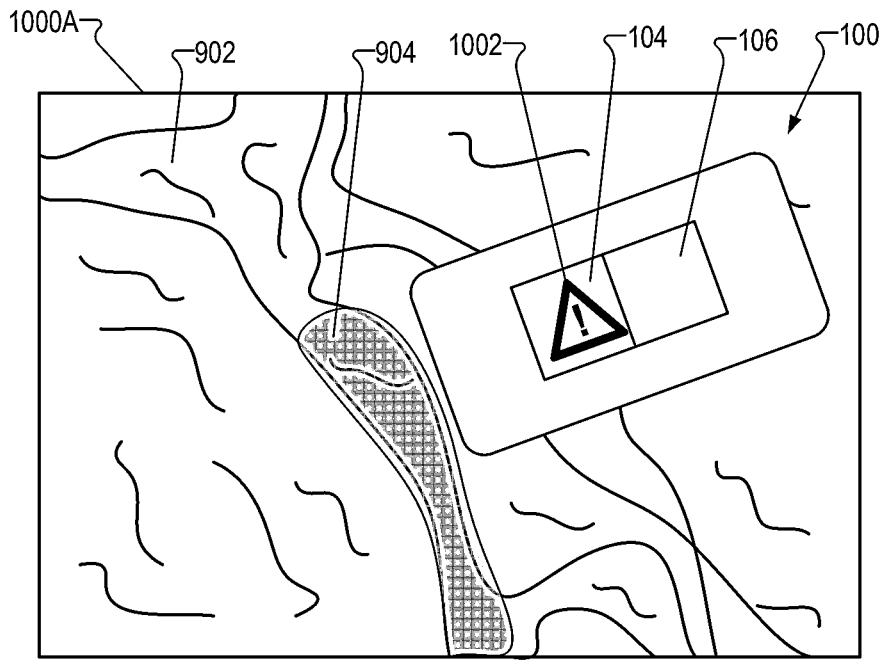

FIG. 10A shows another illustrative fluorescence image 1000A that includes a displayed indication of the measure of photobleaching. Fluorescence image 1000A is similar to fluorescence image 900A except that, in fluorescence image 1000A, a warning icon 1002 is superimposed on first fluorescing region 104 to indicate that first fluorescing region 104 has photobleached beyond a threshold level. It will be recognized that other graphical elements may be used instead of, or in addition to, warning icon 1002, such as a warning message.

Figure 10B:
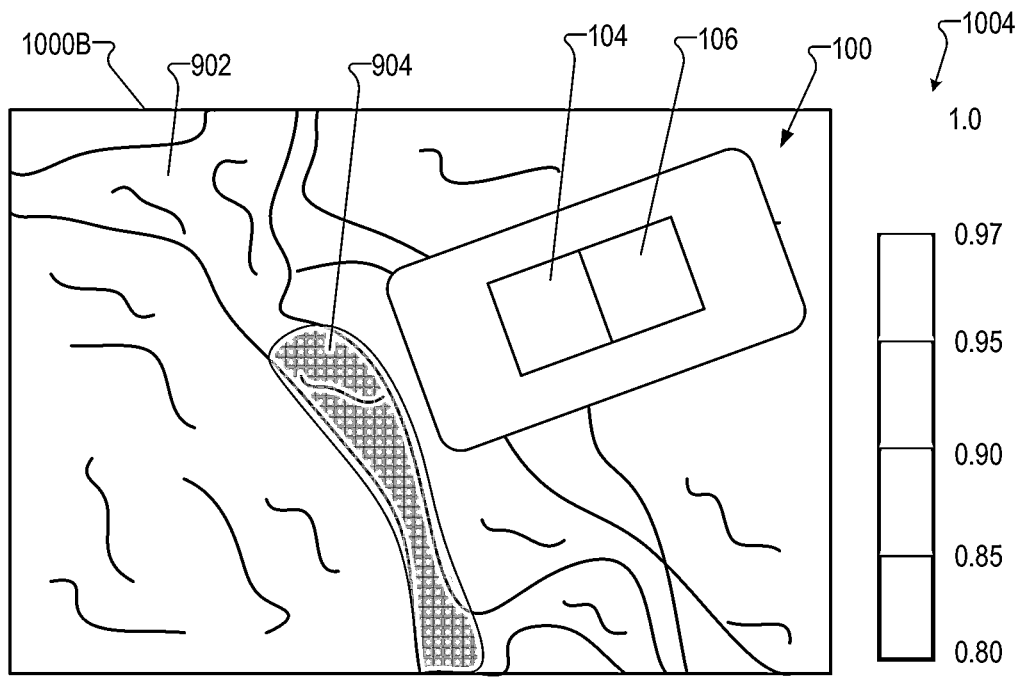

FIG. 10B shows another illustrative fluorescence image 1000B that includes a displayed indication of the measure of photobleaching. Fluorescence image 1000B is similar to fluorescence image 900A except that, in fluorescence image 1000B, pixels corresponding to first fluorescing region 104 are false-colored based on the measure of photobleaching and a color scale 1004 that specifies colors (or shades of a color in a monochromatic image) for different values of the measure of photobleaching. For example, color scale 1004 specifies a range of visible colors ranging from, e.g., yellow (at a target intensity ratio above 0.95), green (at target intensity ratio above 0.90), blue (at a target intensity ratio above 0.85), violet (at a target intensity ratio above 0.80), and red (at a target intensity ratio above 0.75). Pixels that do not detect any fluorescence, or for which the measure of photobleaching is below a threshold level, may be false-colored black or white, for example. Alternatively to using a color scale, system 400 may false-color pixels corresponding to first fluorescing region 104 a first color (e.g., green) when the measure of photobleaching does not satisfy the mitigation condition and may false-color pixels corresponding to first fluorescing region 104 a second color (e.g., blue) when the mitigation condition is satisfied.

In some examples, a photobleaching mitigation operation includes adjusting operation of an imaging device or imaging system. For example, system 400 may direct imaging system 200 to adjust an intensity and/or a peak wavelength of fluorescence excitation illumination 220 to reduce the rate of photobleaching of first fluorescing region 104 and thereby prolong the useful life of fluorescence target 100. Additionally or alternatively, system 400 may automatically turn off a fluorescence imaging modality (e.g., turn off fluorescence detection sensor 210, illumination source 224, and/or processing of fluorescence image data 218 and/or processed image data 226). Alternatively to automatically turning off the fluorescence imaging modality, system 400 may provide a selectable option for a user to manually turn off the fluorescence imaging modality.

In some examples, adjusting operation of an imaging system includes setting and/or adjusting an operating parameter of the imaging system during a calibration procedure. In these examples, a fluorescence target with a known concertation of fluorophores (e.g., in a first fluorescing region) may be used to calibrate the imaging system so that fluorescence emitted from the fluorescence target and/or from objects at the imaged scene (e.g., tissue or a tissue phantom) is detected and displayed correctly. To this end, system 400 uses the measure of photobleaching to set and/or adjust a previously-set operating parameter of the imaging system. Operating parameters of the imaging system that may be set and/or adjusted during a calibration procedure based on the measure of photobleaching include, without limitation, a digital gain applied to detected fluorescence, false coloring of detected fluorescence, an intensity level of fluorescence excitation illumination, and/or a peak or center wavelength of fluorescence excitation illumination. In some examples, the determined measure of photobleaching is used to ensure that the fluorescence target has not photobleached to such a degree that the fluorescence target should not be used for calibration. For example, if the measure of photobleaching satisfies a mitigation condition (e.g., is less than a threshold level), system 400 may terminate the calibration procedure, warn the user, and/or reset all operating parameters previously set or adjusted during the calibration procedure.

In further examples, a photobleaching mitigation operation includes adjusting, based on one or more measures of photobleaching of first fluorescing region 104, fluorescence images depicting first fluorescing region 104. System 400 may adjust fluorescence images in any suitable way. In some examples, system 400 adjusts the signal levels of all or a portion of pixels corresponding to first fluorescing region 104 based on the determined measure of photobleaching. System 400 provides the adjusted fluorescence image data for display by a display device.

In some examples, system 400 assumes that all of first fluorescing region 104 has a same history of exposure to fluorescence excitation illumination and, thus, all of first fluorescing region 104 has the same photobleaching history. Accordingly, system 400 adjusts the signal level of all pixels corresponding to first fluorescing region 104 similarly (e.g., with a same correction factor). For example, system 400 may analyze the target fluorescence image using image processing and/or computer vision techniques to identify first fluorescing region 104. System 400 may determine, based on the measure of photobleaching, a correction factor to adjust the signal level of the pixels corresponding to first fluorescing region 104 to a reference signal level (e.g., the reference intensity level, an intensity level of a non-photobleached state, etc.). The correction factor may be determined in any suitable way. In some examples, system 400 compares the detected target intensity value at the first target position with the detected reference intensity value at the first reference position to determine the correction factor.

For example, with reference to FIG. 3B, at the reference time (10 seconds) the reference intensity value at the first reference position (first position 304-1A) is 0.12. At a target time of 100 seconds (corresponding to a target intensity ratio of 0.978), the target intensity value at the first target position (first position 304-1A) is 0.088. Thus the correction factor is 1.36. At a target time of about 200 seconds (corresponding to a target intensity ratio of 0.962), the target intensity value at the first target position is about 0.068, and thus the correction factor is 1.76. In other examples, system 400 accesses a lookup table or applies a model that correlates target intensity ratios (or other measure of photobleaching) to correction factors. System 400 uses the correction factor to adjust all pixels corresponding to first fluorescing region 104. In this way, system 400 digitally reconstructs fluorescence signal levels in fluorescence images to display an ideal (e.g., unphotobleached) fluorescence target 100 even when fluorescence target 100 has photobleached.

In other examples, the entirety of first fluorescing region 104 is not assumed to have the same exposure to fluorescence excitation illumination. For example, fluorescence target 100 and/or the imaging device may be moved around at the scene over time and thus different parts of first fluorescing region 104 may be exposed to different amounts of fluorescence excitation illumination. System 400 may detect movement of fluorescence target 100 and/or the imaging device (e.g., by kinematic data and/or image data) and determine that the entire first fluorescing region 104 is not assumed to have the same measure of photobleaching. Accordingly, system 400 modifies the fluorescence signal levels of pixels corresponding to first fluorescing region 104 based on multiple different measures of photobleaching determined from multiple different positions corresponding to first fluorescing region 104. In some examples, system 400 may sub-divide first fluorescing region 104 into a plurality of sub-regions and determine a correction factor for each sub-region. Additionally or alternatively, system 400 may determine, by interpolation of multiple different measures of photobleaching, correction factors for pixels not analyzed by system 400.

Figure 11:
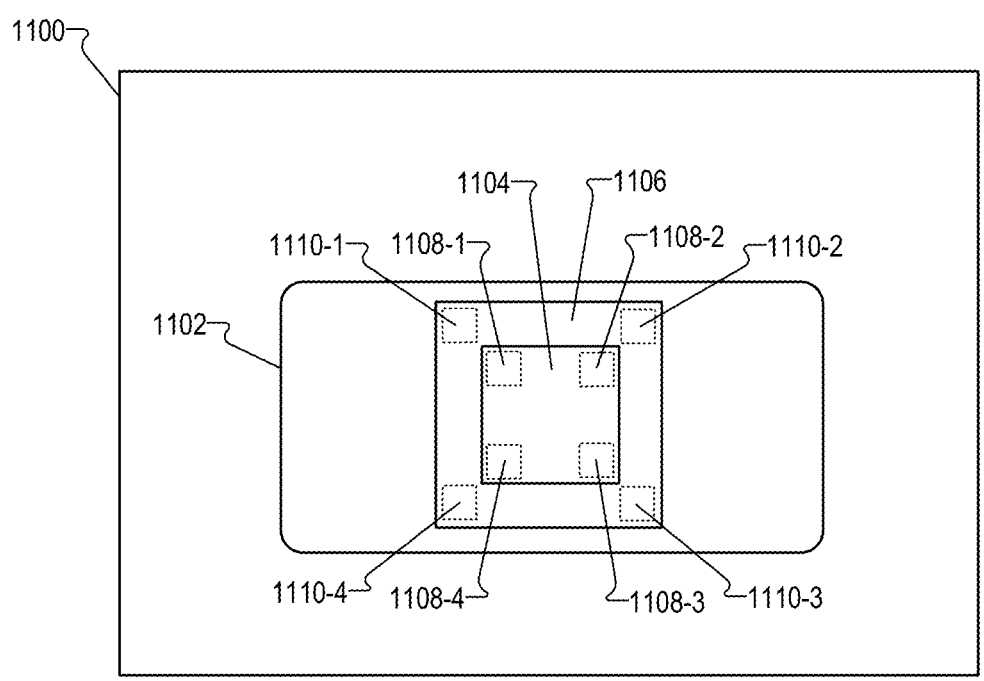
FIG. 11 shows an illustrative fluorescence image depicting an illustrative fluorescence target in which a first fluorescing region is surrounded by a second fluorescing region.

For example, FIG. 11 shows an illustrative fluorescence image 1100 depicting an illustrative fluorescence target 1102 in which a first fluorescing region 1104 is surrounded by a second fluorescing region 1106. System 400 determines a measure of photobleaching of first fluorescing region 1104 at each of a plurality of positions 1108 (e.g., a position 1108-1, a position 1108-2, a position 1108-3, and a position 1108-4) within fluorescence image 1100 and corresponding to first fluorescing region 1104. Positions 1108 are located opposite a plurality of positions 1110 (e.g., a position 1110-1, a position 1110-2, a position 1110-3, and a position 1110-4) within fluorescence image 1100 and corresponding to second fluorescing region 1106.

While positions 1108 and positions 1110 are shown to be located corresponding to corners of first fluorescing region 1104 and second fluorescing region 1106, positions 1108 and 1110 may alternatively be located at any other suitable location, such as at the center of edges of first fluorescing region 1104. Moreover, system 400 may use any other number of positions 1108 as may suit a particular implementation, such as two or three or more than four. In some examples, positions 1108 are located along substantially the entire boundary between first fluorescing region 1104 and second fluorescing region 1106, which may improve the precision and accuracy of determining (e.g., interpolating) the correction factor data at non-analyzed positions of first fluorescing region 1104. Furthermore, first fluorescing region 1104 and second fluorescing region 1106 may have any other shape and configuration as may suit a particular implementation.

Based on the measure of photobleaching determined for each position 1108, system 400 determines (e.g., by interpolation) a measure of photobleaching at one or more other positions (e.g., pixels or groups of pixels) corresponding to the interior (e.g., non-analyzed positions) of first fluorescing region 1104 (e.g., other positions between positions 1108). System 400 determines a correction factor at each interior position in any way described above (e.g., based on the corresponding reference intensity value or based on a lookup table or a model) and corrects pixels based on the associated correction factor.

Determination of the correction factor and adjustment of pixel values of a fluorescence image may be performed with any suitable frequency. For example, each fluorescence image in a fluorescence video stream may be analyzed and modified to digitally reconstruct first fluorescing region 1104. Alternatively, every nth image (where n is an integer such as 3, 5, 10, 24, etc.) of a fluorescence video stream may be analyzed to determine correction factors, which may be used to modify each fluorescence image in a set of n consecutive fluorescence images.

In some examples, the signal levels of the pixels are adjusted until the noise generated by the signal level adjustment is too high, at which point system 400 terminates the signal level adjustment and performs another photobleaching mitigation operation. For example, system 400 may measure a signal-to-noise ratio (SNR) of pixels of the adjusted fluorescence image. System 400 may determine that a second mitigation condition is satisfied when the SNR of the adjusted pixels (e.g., an average, median, maximum, or minimum SNR of all of the adjusted pixels, or the SNR of a predetermined number of the adjusted pixels) is less than a threshold value (a second mitigation condition). In response to determining that the second mitigation condition is satisfied, system 400 may terminate the adjustment of the pixels and perform a second photobleaching mitigation operation (e.g., display a graphical indication of the measure of photobleaching).

In some examples, adjusting the signal level of fluorescence image data may be used to simulate fluorescence from fluorophores in a non-photobleached state even though the fluorophores have photobleached to some degree. For instance, system 400 may estimate, based on the determined measure of photobleaching of the first population of fluorophores (e.g., first fluorescing region 104), target fluorescence signal levels that would be detected from the fluorophores in a non-photobleached state. System 400 may estimate the target fluorescence signal levels in any suitable way. For example, system 400 may estimate the target fluorescence signal levels to be the actual fluorescence signal levels detected at a reference time corresponding to a non-photobleached state of the fluorophores (e.g., an initial use of fluorescence target 100 or a reference time at which the target intensity ratio exceeds a threshold level (e.g., 0.99)). Alternatively, system 400 may estimate the target fluorescence signal levels based on a known reference signal level (e.g., a signal level stored in memory 402 and/or accessed by system 400).

Based on the estimated target fluorescence signal levels, system 400 adjusts the actual signal levels of the fluorescence image data to simulate fluorescence from the fluorophores in a non-photobleached state. For example, system 400 may determine, based on the actual signal levels of the captured fluorescence image data and the estimated target fluorescence signal levels and/or based on a lookup table, correction factors to apply to the actual signal levels of the captured fluorescence image data. System 400 may correct (e.g., increase) the actual signal levels of the captured fluorescence image data with the correction factor to thereby simulate fluorescence from fluorophores in a non-photobleached state. The correction factors may be updated over time as the fluorophores continue to photobleach.

In some examples, the adjusting of the fluorescence image data is performed continually based on the measure of photobleaching. In other examples, the adjusting of the fluorescence image data is performed in response to a determination that a mitigation condition is satisfied (e.g., the target intensity ratio falls below a first threshold level). In further examples, the adjusting of the fluorescence image continues until a mitigation condition is satisfied (e.g., the target intensity ratio falls below a second threshold level and/or the SNR of the adjusted fluorescence image data falls below a threshold level).

In the examples described above, signal levels of pixels in fluorescence images are adjusted based on the measure of photobleaching determined according to method 500. However, signal levels of pixels in fluorescence images may be adjusted based on a measure of photobleaching determined in any other suitable way. For example, the measure of photobleaching may be determined based on a comparison of the target intensity level of fluorescence emitted from a fluorescence target with a known reference intensity level. The known reference intensity level may be determined (e.g., empirically) from one or more unbleached (e.g., new) fluorescence targets. In some examples, system 400 may determine the measure of photobleaching of a fluorescence target by accessing a lookup table that correlates levels of detected fluorescence intensity with different measures of photobleaching.

Various modifications may be made to the apparatuses, systems, and methods described above. For example, fluorescence target 100 may have various other configurations of first fluorescing region 104 and second fluorescing region 106 as may suit a particular implementation. Various configurations of a fluorescence target are shown in FIGS. 12A to 13B.

Figure 12A:
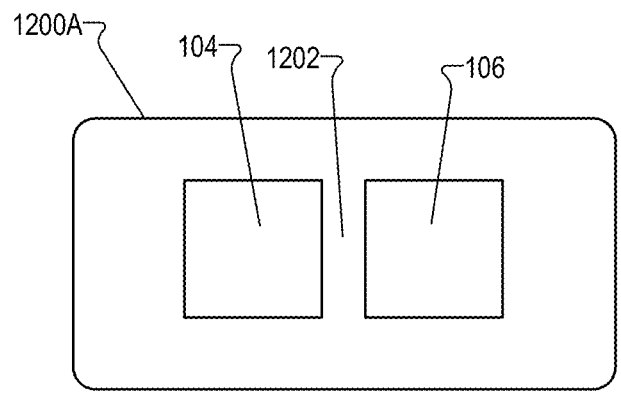
FIGS. 12A-12C and 13A-13B show various different illustrative fluorescence targets.

FIG. 12A shows another illustrative fluorescence target 1200A. Fluorescence target 1200A is similar to fluorescence target 100 except that, in fluorescence target 1200A, first fluorescing region 104 and second fluorescing region 106 are separated from one another by a non-fluorescing boundary region 1202 (e.g., substrate 102). Boundary region 1202 prevents the diffusion of fluorophore particles and/or photons of fluorescence excitation illumination across boundary region 1202 from first fluorescing region 104 to second fluorescing region 106, and vice versa. Boundary region 1202 may also help system 400 detect the boundary between first fluorescing region 104 and second fluorescing region 106.

Figure 12B:
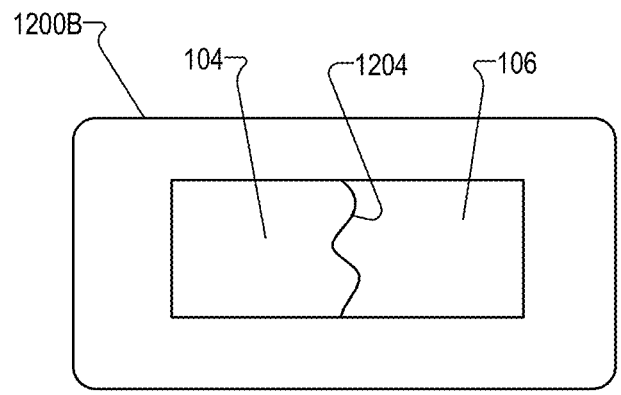

FIG. 12B shows another illustrative fluorescence target 1200B. Fluorescence target 1200B is similar to fluorescence target 100 except that, in fluorescence target 1200B, a boundary 1204 between first fluorescing region 104 and second fluorescing region 106 is not a straight line, which may facilitate detection of boundary 1204 by system 400. As shown, boundary 1204 is curved, although boundary 1204 may have any other configuration that is not straight.

Figure 12C:
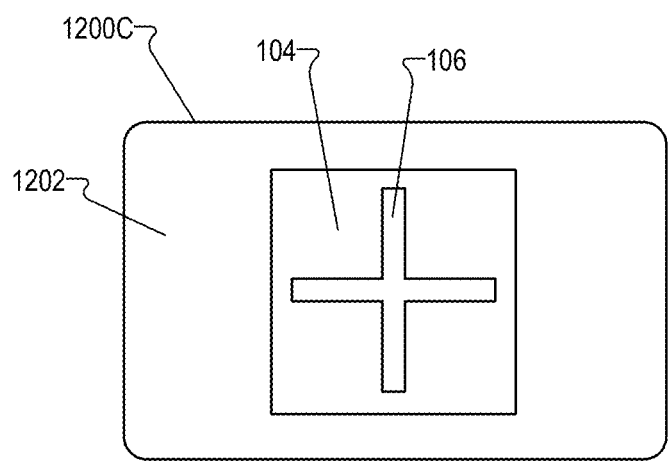

FIG. 12C shows another illustrative fluorescence target 1200C. Fluorescence target 1200C is similar to fluorescence target 100 except that, in fluorescence target 1200C, second fluorescing region 106 is formed within first fluorescing region 104. As shown, second fluorescing region 106 has a cross-hairs shape, although second fluorescing region 106 may have any other suitable shape, such as an oval, an x-shape, or a T-shape. Moreover, fluorescence target 1200C may have multiple different second fluorescing regions 106 within first fluorescing region 104. The shape and configuration of second fluorescing region 106 may be configured to be recognizable by computer vision and may facilitate the determination of a measure of photobleaching at multiple different positions.

Figure 13A:
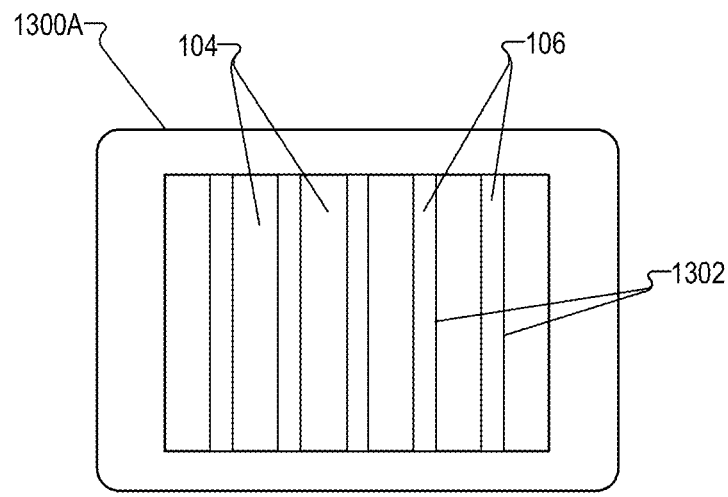

FIG. 13A shows an illustrative fluorescence target 1300A. Fluorescence target 1300A is similar to fluorescence target 100 except that, in fluorescence target 1300A, a plurality of second fluorescing regions 106 are formed by lines 1302 that cross first fluorescing region 104. While FIG. 13A shows that lines 1302 are equally sized and uniformly spaced, lines 1302 may each have any other size and/or spacing as may serve a particular implementation. Lines 1302 may also be non-straight (e.g., curved). In some examples, second fluorescing region 106 is configured to form a two-dimensional bar code or a three-dimensional code (e.g., a QR code) that may be detected by computer vision techniques.

Figure 13B:
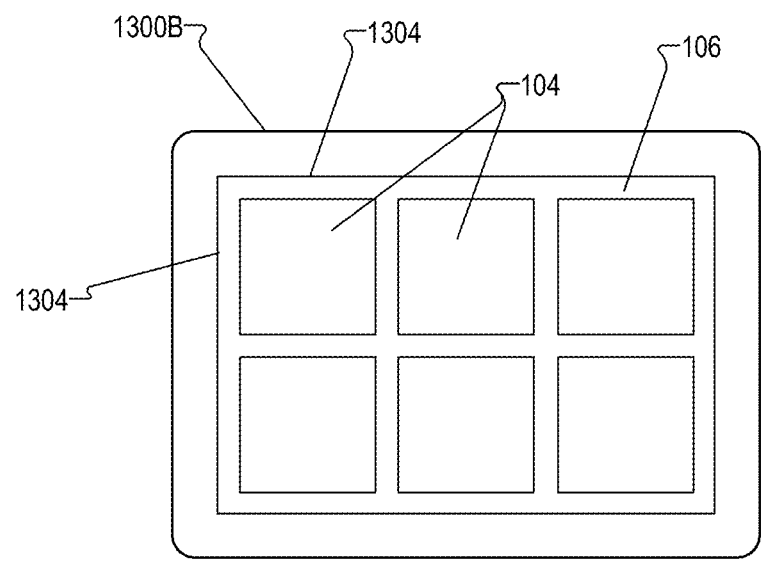

FIG. 13B shows an illustrative fluorescence target 1300B. Fluorescence target 1300B is similar to fluorescence target 100 except that, in fluorescence target 1300B, an array of first fluorescing regions 104 are each bounded by horizontal and vertical lines 1304 forming second fluorescing region 106. In this way, system 400 may easily determine a measure of photobleaching at a plurality of locations corresponding to first fluorescing regions 104. For example, system 400 may determine a measure of photobleaching at each of four positions corresponding to each first fluorescing region 104, as described above regarding fluorescence target 1102. In further examples, system 400 may determine a measure of photobleaching at a high density (e.g., at each position of a plurality of positions located along substantially the entire boundary between each first fluorescing region 104 and each second fluorescing region 106). In this way, a measure of photobleaching and/or a correction factor may be determined with high precision and accuracy at all pixels of fluorescence target 1300A corresponding to first fluorescing regions 104.

In some examples, system 400 may determine the measure of photobleaching of first fluorescing region 104 based on fluorescence detected from multiple different positions. In the examples described above, the measure of photobleaching is determined based on only one set of positions (e.g., first position 304-1A in first fluorescing region 104 and second position 304-1B in second fluorescing region 106 of FIG. 3A). However, as explained above with reference to FIGS. 3A and 3B, different locations on first fluorescing region 104 may have a different of exposure to fluorescence excitation illumination. Accordingly, in some examples system 400 determines the measure of photobleaching at each of multiple different locations corresponding to first fluorescing region 104 (e.g., at each position 1108 in FIG. 11). System 400 determines the measure of photobleaching of first fluorescing region 104 as a whole as the average, median, maximum, minimum, or a weighted combination of the various different measures of photobleaching.

In some examples, system 400 determines a measure of photobleaching at each of a plurality of different positions, as mentioned above, and then performs a photobleaching mitigation operation (operation 518) only when the mitigation condition is satisfied (operation 516) for each of a predetermined number of the positions. For instance, system 400 may perform a photobleaching mitigation operation only when the measure of photobleaching for all positions (e.g., all positions 1108 in FIG. 11) satisfy the mitigation condition. Alternatively, system 400 may perform a photobleaching mitigation operation only when the measure of photobleaching for a majority of positions (e.g., at least three of positions 1108 in FIG. 11) satisfy the mitigation condition.

In further examples, system 400 performs a photobleaching mitigation operation only for local areas that satisfy the mitigation condition. For example, as shown in FIG. 13B, system 400 may separately determine a measure of photobleaching for each first fluorescing region 104. System 400 may separately perform a photobleaching mitigation operation (e.g., display a graphical indication or correct the signal level for the corresponding pixels) for each first fluorescing region 104 for which the measure of photobleaching satisfies a mitigation condition.

In yet further examples, adjustment of the second target intensity value may be omitted in operation 506 and in operation 512. For example, the measure of photobleaching may be determined by comparing the target intensity ratio with the reference intensity ratio. To illustrate with reference to FIG. 3B, the reference intensity ratio at the reference time (10 seconds) is 2.0 (0.12 divided by 0.06) and the target intensity ratio at a target time of 100 seconds is 1.956 (0.088 divided by 0.045). System 400 may determine the measure of photobleaching as the ratio of the target intensity ratio to the reference intensity ratio (0.978), or any other suitable measure based on the target intensity ratio and the reference intensity ratio.

In other examples, system 400 may perform a noise reduction operation to reduce noise in the acquired data that system 400 uses to determine the measure of photobleaching. The noise in the acquired signal is evident from curve 802 in FIG. 8. To reduce noise, system 400 may use any suitable technique on the detected fluorescence signal (e.g., fluorescence image data 218), such as temporal filtering or image denoising. Additionally or alternatively, system 400 may analyze fluorescence at groups of pixels rather than individual pixels.

In some examples, a measure of photobleaching includes a measure of photobleaching history of the first fluorescing region. A measure of photobleaching history of the first fluorescing region may include a temporal log or account of levels of multiple measures of photobleaching of the first fluorescing region at various points in time. For example, system 400 may continually or periodically determine a measure of photobleaching (e.g., by any of the methods described above) and log each measure of photobleaching (e.g., in memory 402). System 400 may perform a mitigation operation (e.g., operation 518, operation 610, and/or operation 612) based on the measure of photobleaching history, such as based on an average or a rolling average of multiple logged measures of photobleaching. Additionally or alternatively, system 400 may determine that a mitigation condition is satisfied (e.g. in operation 516, operation 606, and/or operation 612) when a threshold number of logged measures of photobleaching satisfy the mitigation condition.

In some examples, the measure of photobleaching history (e.g., multiple measures of photobleaching at various different points in time) of a particular fluorescence target may be tracked over multiple different uses (e.g., surgical procedures, training procedures, calibration procedures, etc.). In these examples, the fluorescence target may include an identifier that may be read by system 400 to associate the measure of photobleaching history with the particular fluorescence target. In some examples, the identifier is a visual identifier that system 400 may read, such as a visual tag (e.g., a textual identifier and/or a graphical identifier) that may be identified by computer vision, a two-dimensional code (e.g., a barcode), and/or a three-dimensional code (e.g., a QR code). Additionally or alternatively, the identifier may be a radio frequency identification (RFID) tag. By tracking measures of photobleaching of the fluorescence target at various points in time over multiple different uses, early discarding of the fluorescence target can be prevented and the fluorescence target can be effectively used throughout the duration of its useful life.

In some examples, system 400 may determine, in addition or alternatively to determining a measure of photobleaching of first fluorescing region 104, a measure of photobleaching of second fluorescing region 106. System 400 may determine the measure of photobleaching of second fluorescing region 106 in the same or a similar manner as described above with respect to first fluorescing region 104. Method 500 may be applied to second fluorescing region 106. For example, system 400 may perform one or more mitigation operations based on a measure of photobleaching of second fluorescing region 106. For instance, system 400 may adjust signal levels of pixels corresponding to second fluorescing region 106.

The apparatuses, systems, and methods described herein have been described with reference to fluorescence. However, it will be appreciated that the systems and methods described herein are not limited to fluorescence but may be applied to any other type of luminescence, including but not limited to photoluminescence (e.g., phosphorescence, etc.), electroluminescence, chemiluminescence, mechanoluminescence, radioluminescence, and the like.

Figure 14:
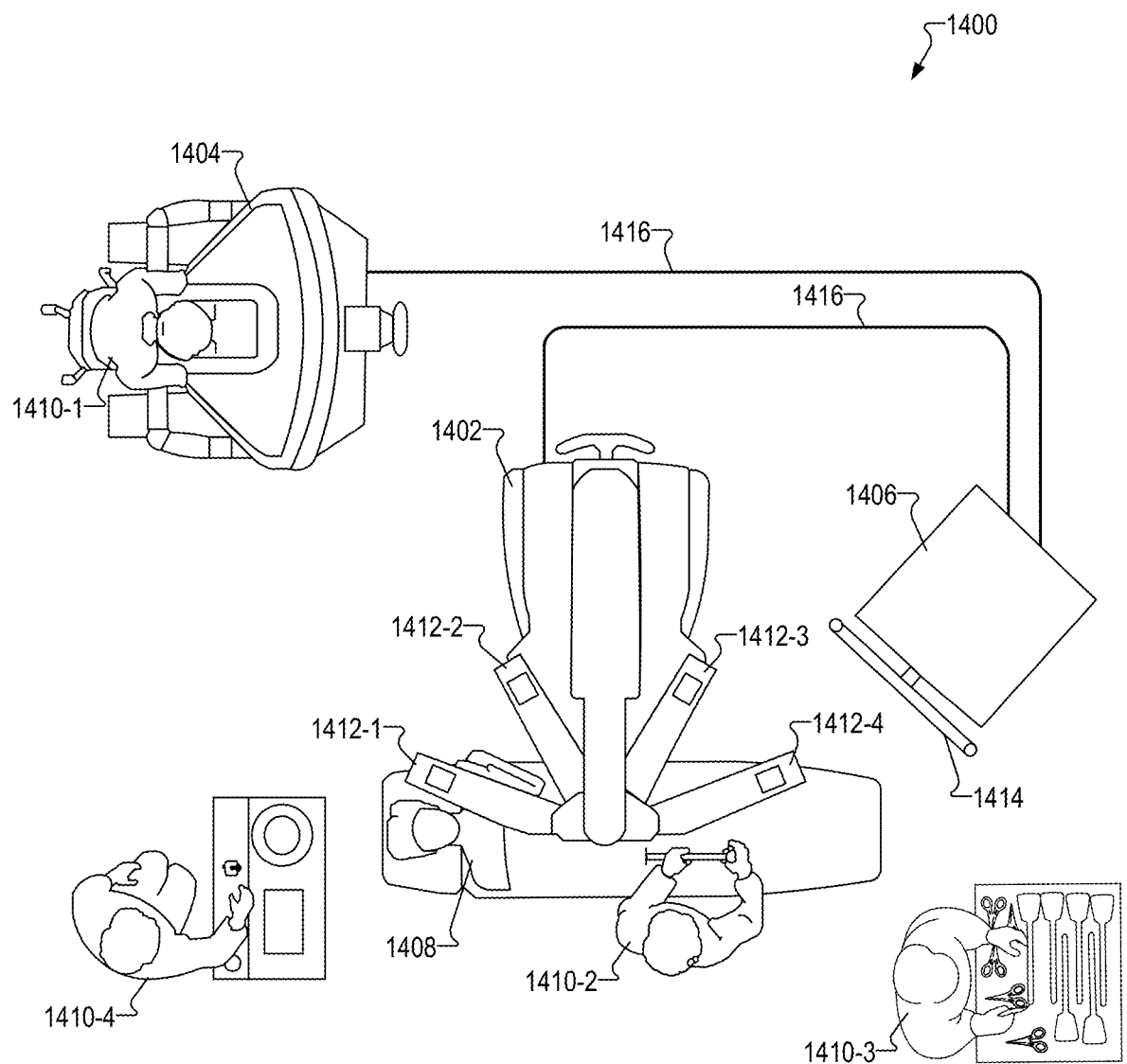
FIG. 14 shows an illustrative computer-assisted surgical system.

FIG. 14 shows an illustrative computer-assisted surgical system 1400 ("surgical system 1400") that may be used in conjunction with the apparatuses, systems, and methods described herein. As described herein, system 400 may be implemented by surgical system 1400, connected to surgical system 1400, and/or otherwise used in conjunction with surgical system 1400.

As shown, surgical system 1400 includes a manipulating system 1402, a user control system 1404, and an auxiliary system 1406 communicatively coupled one to another. Surgical system 1400 may be utilized by a surgical team to perform a computer-assisted surgical procedure on a subject 1408. As shown, the surgical team may include a surgeon 1410-1, an assistant 1410-2, a nurse 1410-3, and an anesthesiologist 1410-4, all of whom may be collectively referred to as "surgical team members 1410." Additional or alternative surgical team members may be present during a surgical session as may serve a particular implementation.

While FIG. 14 illustrates an ongoing minimally invasive surgical procedure, it will be understood that surgical system 1400 may similarly be used to perform open surgical procedures or other types of surgical procedures that may similarly benefit from the accuracy and convenience of surgical system 1400. Additionally, it will be understood that the surgical session throughout which surgical system 1400 may be employed may not only include an operative phase of a surgical procedure, as is illustrated in FIG. 14, but may also include preoperative, postoperative, and/or other suitable phases of the surgical procedure. A surgical procedure may include any procedure in which manual and/or instrumental techniques are used on a subject to investigate, diagnose, and/or treat a physical condition of the subject. Additionally, a surgical procedure may include any non-clinical procedure, e.g., a procedure that is not performed on a live subject, such as a calibration or testing procedure, a training procedure, and an experimental or research procedure.

As shown in FIG. 14, manipulating system 1402 includes a plurality of manipulator arms 1412 (e.g., manipulator arms 1412-1 through 1412-4) to which a plurality of surgical instruments may be coupled. Each surgical instrument may be implemented by any suitable surgical tool (e.g., a tool having tissue-interaction functions), medical tool, imaging device (e.g., an endoscope), sensing instrument (e.g., a force-sensing surgical instrument), diagnostic instrument, or the like that may be used for a computer-assisted surgical procedure on subject 1408 (e.g., by being at least partially inserted into subject 1408 and manipulated to perform a computer-assisted surgical procedure on subject 1408). While manipulating system 1402 is depicted and described herein as including four manipulator arms 1412, manipulating system 1402 may include only a single manipulator arm 1412 or any other number of manipulator arms as may serve a particular implementation.

Manipulator arms 1412 and/or surgical instruments attached to manipulator arms 1412 may include one or more displacement transducers, orientational sensors, and/or positional sensors used to generate raw (i.e., uncorrected) kinematics information. One or more components of surgical system 1400 may be configured to use the kinematics information to track (e.g., determine positions and orientations of) and/or control the surgical instruments.

User control system 1404 is configured to facilitate control by surgeon 1410-1 of manipulator arms 1412 and surgical instruments attached to manipulator arms 1412. For example, surgeon 1410-1 may interact with user control system 1404 to remotely move or manipulate manipulator arms 1412 and the surgical instruments. To this end, user control system 1404 provides surgeon 1410-1 with images (e.g., high-definition 3D images, composite medical images, and/or fluorescence images) of a surgical area associated with subject 1408 as captured by an imaging system (e.g., imaging system 200). In certain examples, user control system 1404 includes a stereo viewer having two displays where stereoscopic images of a surgical area associated with subject 1408 and generated by a stereoscopic imaging system may be viewed by surgeon 1410-1. Surgeon 1410-1 may utilize the images to perform one or more procedures with one or more surgical instruments attached to manipulator arms 1412.

To facilitate control of surgical instruments, user control system 1404 includes a set of master controls. The master controls may be manipulated by surgeon 1410-1 to control movement of surgical instruments (e.g., by utilizing robotic and/or teleoperation technology). The master controls may be configured to detect a wide variety of hand, wrist, and finger movements by surgeon 1410-1. In this manner, surgeon 1410-1 may intuitively perform a procedure using one or more surgical instruments.

Auxiliary system 1406 includes one or more computing devices configured to perform primary processing operations of surgical system 1400. In such configurations, the one or more computing devices included in auxiliary system 1406 may control and/or coordinate operations performed by various other components (e.g., manipulating system 1402 and user control system 1404) of surgical system 1400. For example, a computing device included in user control system 1404 may transmit instructions to manipulating system 1402 by way of the one or more computing devices included in auxiliary system 1406. As another example, auxiliary system 1406 may receive, from manipulating system 1402, and process image data (e.g., fluorescence image data 218 and/or processed fluorescence image data 226) representative of images captured by an imaging device (e.g., imaging device 202) attached to one of manipulator arms 1412.

In some examples, auxiliary system 1406 is configured to present visual content to surgical team members 1410 who may not have access to the images provided to surgeon 1410-1 at user control system 1404. To this end, auxiliary system 1406 may include a display monitor 1414 configured to display one or more user interfaces, such as images (e.g., 2D images, composite medical images, and/or fluorescence images) of the surgical area, information associated with subject 1408 and/or the surgical procedure, and/or any other visual content as may serve a particular implementation. For example, display monitor 1414 may display images of the surgical area together with additional content (e.g., graphical content, contextual information, etc.) concurrently displayed with the images. In some embodiments, display monitor 1414 is implemented by a touchscreen display with which surgical team members 1410 may interact (e.g., by way of touch gestures) to provide user input to surgical system 1400.

Manipulating system 1402, user control system 1404, and auxiliary system 1406 may be communicatively coupled one to another in any suitable manner. For example, as shown in FIG. 14, manipulating system 1402, user control system 1404, and auxiliary system 1406 are communicatively coupled by way of control lines 1416, which may represent any wired or wireless communication link as may serve a particular implementation. To this end, manipulating system 1402, user control system 1404, and auxiliary system 1406 may each include one or more wired or wireless communication interfaces, such as one or more local area network interfaces, Wi-Fi network interfaces, cellular interfaces, etc.

In some examples, a non-transitory computer-readable medium storing computer-readable instructions may be provided in accordance with the principles described herein. The instructions, when executed by a processor of a computing device, may direct the processor and/or computing device to perform one or more operations, including one or more of the operations described herein. Such instructions may be stored and/or transmitted using any of a variety of known computer-readable media.

A non-transitory computer-readable medium as referred to herein may include any non-transitory storage medium that participates in providing data (e.g., instructions) that may be read and/or executed by a computing device (e.g., by a processor of a computing device). For example, a non-transitory computer-readable medium may include, but is not limited to, any combination of non-volatile storage media and/or volatile storage media. Exemplary non-volatile storage media include, but are not limited to, read-only memory, flash memory, a solid-state drive, a magnetic storage device (e.g. a hard disk, a floppy disk, magnetic tape, etc.), ferroelectric random-access memory ("RAM"), and an optical disc (e.g., a compact disc, a digital video disc, a Blu-ray disc, etc.). Exemplary volatile storage media include, but are not limited to, RAM (e.g., dynamic RAM).

Figure 15:
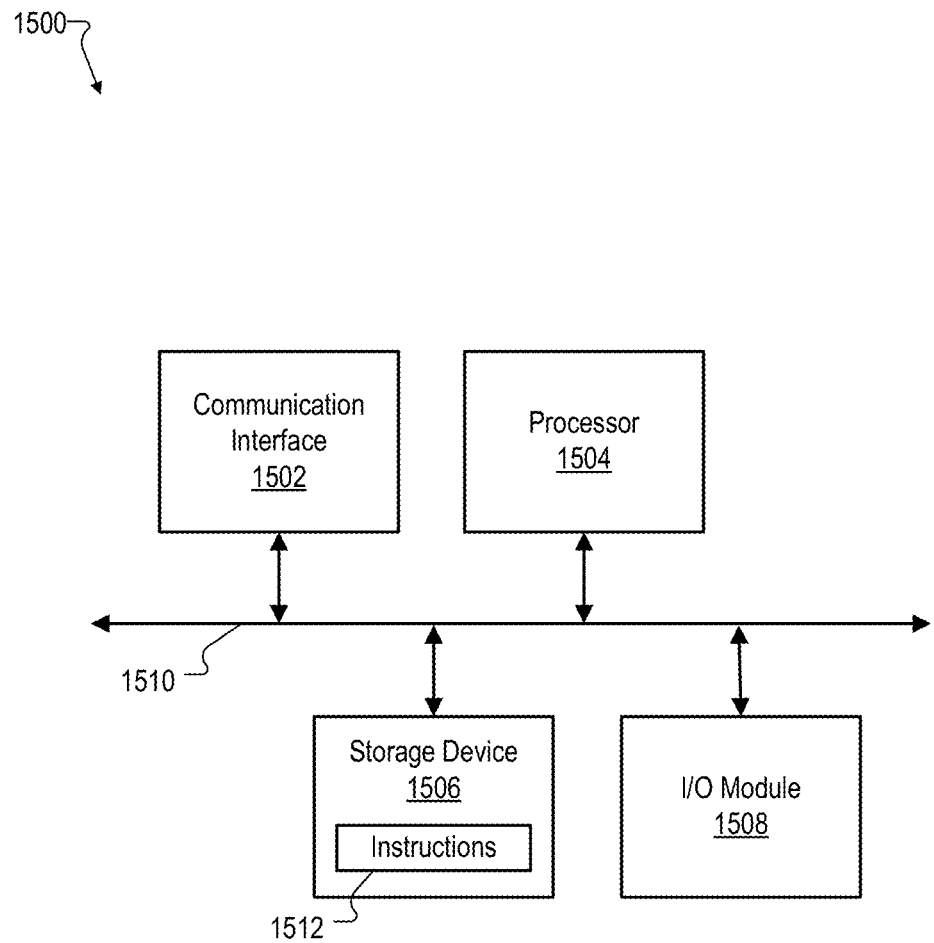
FIG. 15 shows a functional diagram of an illustrative computing device.

FIG. 15 shows a functional diagram of an illustrative computing device 1500 that may be specifically configured to perform one or more of the processes described herein. Any of the systems, units, computing devices, and/or other components described herein may be implemented by computing device 1500.

As shown in FIG. 15, computing device 1500 may include a communication interface 1502, a processor 1504, a storage device 1506, and an input/output ("I/O") module 1508 communicatively connected one to another via a communication infrastructure 1510. While an exemplary computing device 1500 is shown in FIG. 15, the components illustrated in FIG. 15 are not intended to be limiting. Additional or alternative components may be used in other embodiments. Components of computing device 1500 shown in FIG. 15 will now be described in additional detail.

Communication interface 1502 may be configured to communicate with one or more computing devices. Examples of communication interface 1502 include, without limitation, a wired network interface (such as a network interface card), a wireless network interface (such as a wireless network interface card), a modem, an audio/video connection, and any other suitable interface.

Processor 1504 generally represents any type or form of processing unit capable of processing data and/or interpreting, executing, and/or directing execution of one or more of the instructions, processes, and/or operations described herein. Processor 1504 may perform operations by executing computer-executable instructions 1512 (e.g., an application, software, code, and/or other executable data instance) stored in storage device 1506.

Storage device 1506 may include one or more data storage media, devices, or configurations and may employ any type, form, and combination of data storage media and/or device. For example, storage device 1506 may include, but is not limited to, any combination of the non-volatile media and/or volatile media described herein. Electronic data, including data described herein, may be temporarily and/or permanently stored in storage device 1506. For example, data representative of computer-executable instructions 1512 configured to direct processor 1504 to perform any of the operations described herein may be stored within the storage device 1506. In some examples, data may be arranged in one or more databases residing within storage device 1506.

I/O module 1508 may include one or more I/O modules configured to receive user input and provide user output. I/O module 1508 may include any hardware, firmware, software, or combination thereof supportive of input and output capabilities. For example, I/O module 1508 may include hardware and/or software for capturing user input, including, but not limited to, a keyboard or keypad, a touchscreen component (e.g., touchscreen display), a receiver (e.g., an RF or infrared receiver), motion sensors, and/or one or more input buttons.

I/O module 1508 may include one or more devices for presenting output to a user, including, but not limited to, a graphics engine, a display (e.g., a display screen), one or more output drivers (e.g., display drivers), one or more audio speakers, and one or more audio drivers. In certain embodiments, I/O module 1508 is configured to provide graphical data to a display for presentation to a user. The graphical data may be representative of one or more graphical user interfaces and/or any other graphical content as may serve a particular implementation.

In the preceding description, various exemplary embodiments have been described with reference to the accompanying drawings. It will, however, be evident that various modifications and changes may be made thereto, and additional embodiments may be implemented, without departing from the scope of the invention as set forth in the claims that follow. For example, certain features of one embodiment described herein may be combined with or substituted for features of another embodiment described herein. The description and drawings are accordingly to be regarded in an illustrative rather than a restrictive sense.

What is claimed is:

1. A system comprising:
a memory storing instructions; and
a processor communicatively coupled to the memory and configured to execute the instructions to:
direct an imaging system to detect, over a period of time, first fluorescence emitted from a first fluorescing region illuminated with fluorescence excitation illumination, the first fluorescing region comprising a first population of fluorophores that emit the first fluorescence, the first fluorescing region photobleaching at a first photobleaching rate;
direct the imaging system to detect, over the period of time, second fluorescence emitted from a second fluorescing region illuminated with the fluorescence excitation illumination, the second fluorescing region comprising a second population of fluorophores that emit the second fluorescence, the second fluorescing region photobleaching at a second photobleaching rate that is different than the first photobleaching rate; and
determine, based on the detected first fluorescence and second fluorescence, a measure of photobleaching of the first fluorescing region.

2. The system of claim 1, wherein the determining the measure of photobleaching of the first fluorescing region comprises:
determining, based on the first fluorescence detected in a reference fluorescence image captured at a reference time, a first reference intensity value at a first reference position corresponding to the first fluorescing region;
determining, based on the second fluorescence detected in the reference fluorescence image, a second reference intensity value at a second reference position corresponding to the second fluorescing region;

determining, based on the first fluorescence detected in a target fluorescence image captured at a target time subsequent to the reference time, a first target intensity value at a first target position corresponding to the first fluorescing region; and determining, based on the second fluorescence detected in the target fluorescence image, a second target intensity value at a second target position corresponding to the second fluorescing region.

3. The system of claim 2, wherein:

the first reference intensity value and the second reference intensity value are normalized to a common intensity value; and the measure of photobleaching of the first fluorescing region comprises a target intensity ratio, the target intensity ratio comprising a ratio of the first target intensity value to the second target intensity value.

4. The system of claim 2, wherein the determining the measure of photobleaching further comprises:

identifying, in the reference fluorescence image, a boundary between the first fluorescing region and the second fluorescing region;

identifying, based on the boundary in the reference fluorescence image, the first reference position and the second reference position;

identifying, in the target fluorescence image, the boundary between the first fluorescing region and the second fluorescing region; and identifying, based on the boundary in the target fluorescence image, the first target position and the second target position.

5. The system of claim 1, wherein the processor is further configured to execute the instructions to perform a photobleaching mitigation operation based on the determined measure of photobleaching.

6. The system of claim 5, wherein:

the processor is further configured to execute the instructions to determine that the measure of photobleaching of the first fluorescing region satisfies a mitigation condition; and the photobleaching mitigation operation is performed in response to the determining that the measure of photobleaching of the first fluorescing region satisfies the mitigation condition.

7. The system of claim 5, wherein the photobleaching mitigation operation comprises at least one of:

providing an indication of the measure of photobleaching of the first fluorescing region; and adjusting operation of the imaging system based on the measure of photobleaching.

8. The system of claim 5, wherein the photobleaching mitigation operation comprises:

adjusting, based on the measure of photobleaching of the first fluorescing region, a signal level of fluorescence image data representative of a fluorescence image depicting the first fluorescence; and providing the adjusted fluorescence image data for display by a display device.

9. A method comprising:

directing, by a fluorescence imaging control system, an imaging system to detect, over a period of time, first fluorescence emitted from a first fluorescing region illuminated with fluorescence excitation illumination, the first fluorescing region comprising a first population of fluorophores that emit the first fluorescence, the first fluorescing region photobleaching at a first photobleaching rate;

directing, by the fluorescence imaging control system, the imaging system to detect, over the period of time, second fluorescence emitted from a second fluorescing region illuminated with the fluorescence excitation illumination, the second fluorescing region comprising a second population of fluorophores that emit the second fluorescence, the second fluorescing region photobleaching at a second photobleaching rate that is slower than the first photobleaching rate; and determining, by the fluorescence imaging control system based on the detected first fluorescence and second fluorescence, a measure of photobleaching of the first fluorescing region.

10. The method of claim 9, wherein the determining the measure of photobleaching of the first fluorescing region comprises:

determining, based on the first fluorescence detected in a reference fluorescence image captured at a reference time, a first reference intensity value at a first reference position corresponding to the first fluorescing region;

determining, based on the second fluorescence detected in the reference fluorescence image, a second reference intensity value at a second reference position corresponding to the second fluorescing region;

determining, based on the first fluorescence detected in a target fluorescence image captured at a target time subsequent to the reference time, a first target intensity value at a first target position corresponding to the first fluorescing region; and determining, based on the second fluorescence detected in the target fluorescence image, a second target intensity value at a second target position corresponding to the second fluorescing region.

11. The method of claim 10, wherein:

the first reference intensity value and the second reference intensity value are normalized to a common intensity value; and the measure of photobleaching of the first fluorescing region comprises a target intensity ratio, the target intensity ratio comprising a ratio of the first target intensity value to the second target intensity value.

12. The method of claim 10, wherein the determining the measure of photobleaching further comprises:

identifying, in the reference fluorescence image, a boundary between the first fluorescing region and the second fluorescing region;

identifying, based on the boundary in the reference fluorescence image, the first reference position and the second reference position;

identifying, in the target fluorescence image, the boundary between the first fluorescing region and the second fluorescing region; and identifying, based on the boundary in the target fluorescence image, the first target position and the second target position.

13. The method of claim 9, further comprising performing, by the fluorescence imaging control system, a photobleaching mitigation operation based on the determined measure of photobleaching.

14. The method of claim 13, further comprising:

determining, by the fluorescence imaging control system, that the measure of photobleaching of the first fluorescing region satisfies a mitigation condition;

wherein the photobleaching mitigation operation is performed in response to the determining that the measure of photobleaching of the first fluorescing region satisfies the mitigation condition.

15. The method of claim 13, wherein the photobleaching mitigation operation comprises at least one of:
providing an indication of the measure of photobleaching of the first fluorescing region; and
adjusting operation of the imaging system based on the measure of photobleaching.

16. The method of claim 13, wherein the photobleaching mitigation operation comprises:
adjusting, based on the measure of photobleaching of the first fluorescing region, a signal level of fluorescence image data representative of a fluorescence image depicting the first fluorescence; and
providing the adjusted fluorescence image data for display by a display device.

17. A system comprising:
a memory storing instructions; and
one or more processors communicatively coupled to the memory and configured to execute the instructions to:
direct an imaging system to detect fluorescence emitted by fluorophores included in a fluorescence target illuminated with fluorescence excitation illumination;
generate, based on the detected fluorescence, fluorescence image data representative of a fluorescence image;
determine that a measure of photobleaching of the fluorophores satisfies a mitigation condition;
adjust, in response to the determining that the measure of photobleaching of the fluorophores satisfies the mitigation condition, the fluorescence image data based on the measure of photobleaching of the fluorophores; and
provide the adjusted fluorescence image data for display by a display device.

18. A system comprising:
a memory storing instructions; and
one or more processors communicatively coupled to the memory and configured to execute the instructions to:
direct an imaging system to detect fluorescence emitted by fluorophores included in a fluorescence target illuminated with fluorescence excitation illumination;
generate, based on the detected fluorescence, fluorescence image data representative of a fluorescence image;
adjust, based on a measure of photobleaching of the fluorophores, the fluorescence image data, wherein adjusting the fluorescence image data comprises:
determining, based on the measure of photobleaching, a correction factor configured to correct a signal level of the fluorescence image data to a reference signal level; and
adjusting the signal level of the fluorescence image data based on the correction factor; and
provide the adjusted fluorescence image data for display by a display device.

19. A system comprising:
a memory storing instructions; and
one or more processors communicatively coupled to the memory and configured to execute the instructions to:
direct an imaging system to detect fluorescence emitted by fluorophores included in a fluorescence target illuminated with fluorescence excitation illumination;
generate, based on the detected fluorescence, fluorescence image data representative of a fluorescence image;
adjust, based on a measure of photobleaching of the fluorophores, the fluorescence image data, wherein adjusting the fluorescence image data comprises:
estimating, based on the measure of photobleaching of the fluorophores, a target fluorescence signal that would be detected from the fluorophores in a non-photobleached state; and
adjusting a signal level of the fluorescence image data to simulate the target fluorescence signal; and
provide the adjusted fluorescence image data for display by a display device.

\* \* \* \* \*